United States Patent
Zanzucchi et al.

[11] Patent Number: 5,985,119
[45] Date of Patent: Nov. 16, 1999

[54] ELECTROKINETIC PUMPING

[75] Inventors: Peter John Zanzucchi, Lawrenceville; Charlotte Anna Burton, Brick; Sterling Edward McBride, Lawrenceville; Satyam Choudary Cherukuri, Cranbury; William Chiang, Monmouth Junction; Aaron W. Levine, Mercer; Richard Morgan Moroney, III, Princeton, all of N.J.

[73] Assignee: Sarnoff Corporation, Princeton, N.J.

[21] Appl. No.: 08/645,966

[22] Filed: May 10, 1996

Related U.S. Application Data

[63] Continuation-in-part of application No. 08/556,036, Nov. 9, 1995, Pat. No. 5,846,396, which is a continuation-in-part of application No. 08/338,703, Nov. 10, 1994, Pat. No. 5,585,069, and a continuation-in-part of application No. 08/469,238, Jun. 6, 1995, Pat. No. 5,632,876, and a continuation-in-part of application No. 08/483,331, Jun. 7, 1995, Pat. No. 5,603,351, and a continuation-in-part of application No. 08/556,423, Nov. 9, 1995, Pat. No. 5,858,193, which is a continuation-in-part of application No. 08/469,238, Jun. 6, 1995, Pat. No. 5,632,876, and a continuation-in-part of application No. 08/483,331, Jun. 7, 1995, Pat. No. 5,603,351.

[51] Int. Cl.⁶ .................................................. G01N 27/26
[52] U.S. Cl. .......................... 204/450; 204/600; 422/129; 422/188
[58] Field of Search .................... 204/450, 600; 422/129, 131, 149, 188

[56] References Cited

U.S. PATENT DOCUMENTS

| | | | |
|---|---|---|---|
| 4,412,785 | 11/1983 | Roman | 417/50 |
| 4,676,274 | 6/1987 | Brown | 137/806 |
| 4,891,120 | 1/1990 | Sethi et al. | 204/299 R |
| 4,908,112 | 3/1990 | Pace | 204/299 |
| 5,053,454 | 10/1991 | Judd | 525/54.11 |
| 5,180,288 | 1/1993 | Richter et al. | 417/48 |
| 5,194,133 | 3/1993 | Clark et al. | 204/299 |
| 5,296,114 | 3/1994 | Manz | 204/180 |
| 5,359,115 | 10/1994 | Campbell et al. | 558/110 |
| 5,384,261 | 1/1995 | Winkler | 436/518 |
| 5,463,564 | 10/1995 | Agrafiotis et al. | 364/496 |
| 5,480,614 | 1/1996 | Kamahori | 422/70 |
| 5,534,328 | 7/1996 | Ashmead et al. | 428/166 |
| 5,580,523 | 12/1996 | Bard | 422/50 |
| 5,639,423 | 6/1997 | Northrup et al. | 422/50 |

FOREIGN PATENT DOCUMENTS

WO 96/04547 2/1996 WIPO.

OTHER PUBLICATIONS

Woolley et al., Ultra–High–Speed DNA Fragment Separations Using Microfabricated Capillary Array Electrophoresis Chips, Proc. Natl. Acad. Sci. USA 91:11348–11352, Nov. 1994.

Dasgupta et al., Electroosmosis: A Reliable Fluid Propulsion System For Flow Injection Analysis, Anal. Chem. 66:1792–1798, 1994 Month Unknown.

Harmon et al., Selectivity in Electrophoretically Mediated Microanalysis By Control of Product Detection Time, Anal. Chem. 66:3797–3805, 1994 Month Unknown.

Patterson, et al., Electrophoretically Mediated Microanalysis of Calcium, Journal of Chromatography A, 662:389–395, 1994 Month Unknown.

Microfabricated Device is Chemistry Lab on a Chip, Chemical & Engineering News, Dec. 12, 1994.

(List continued on next page.)

*Primary Examiner*—Robert Warden
*Assistant Examiner*—Alex Noguerola
*Attorney, Agent, or Firm*—William J. Burke

[57] ABSTRACT

The invention provides methods of performing a synthetic process in a liquid distribution system having reaction cells, by pumping at least one reagent into a reaction cell.

28 Claims, 11 Drawing Sheets

OTHER PUBLICATIONS

Harmon et al., Mathematical Treatment of Electrophoretically Mediated Microanalysis, Anal. Chem. 65:2655–2662, 1993 Month Unknown.

Richeter et al., A Micromachined Electrohydrodynamic (EHD) Pump, Sensors and Actuators A, 29:159–168, 1992 Month Unknown.

Bart et al., Microfabricated Electrohydrodynamic Pumps, Sensors and Actuators, A21–A23:193–197, 1990 Month Unknown.

Melcher, Traveling–Wave Induced Electroconvection, The Physics of Fluids, 9:1548–1555, 1966 Month Unknown.

Pickard, Ion Drag Pumping. II. Experiment, J. Applied Physics, 34:251–258, 1963 Month Unknown.

Stuetzer, Ion Drag Pumps, J. Applied Physics, 31:136–146, 1960 Month Unknown.

Jacobson et al., Precolumn Reactions With Electrophoretic Analysis Integrated on a Microchip, Anal, Chem., 66:4127—4123, 1994 Month Unknown.

Jacobson, et al., Effects of Injection Schemes and Column Geometry on the Performance of Microchip Electrophoresis Devices, Anal. Chem. 1994, 66:1107–1113 Month Unknown.

Jacobson, et al., High–Speed Separations on a Microchip, anal. Chem. 1994, 66:1114–1118 Month Unknown.

Fan, et al., Micromachining of Capillary Electrophoresis Injectors and Separatos on Glass Chips and Evaluation of Flow at Capillary Intersections, Anal. Chem., 1994, 6:177–184 Month Unknown.

Megregany, Microelectromechanical Systems, Circuits and Devices, Jul. 1993.

Harrison, et al., Micromachining a Miniaturized Capillary Electrophoresis–Based Chemical Analysis System on a Chip, Science, vol. 261, Aug. 13, 1993.

Harrison, et al., Capillary Electrophoresis and Sample Injection Systems Integrated on a Planar Glass Chip, Anal. Chem. 1992, 64:1926–1932 Month Unknown.

Fisher, Microchips For Drug Compounds, New York times, Mar. 3, 1991.

Fodor, ete al., Light–Directed, Spatially Addressable Parallel Chemical Synthesis, Research Article, Science, vol. 251, Feb. 15, 1991, pp. 767–773.

The Silver Shotguns, The Economist, Dec. 14–20, 1991.

Howe, et al., Silicon Micromechanics; Sensors and Actuators on a Chip, IEEE Spectrum, Jul. 1990.

Angell, et al., Silicon Micromechanical Devices, Scientific American 248:44–55, 1983 Month Unknown.

Petersen, Silicon as a Mechanical Material, Proceedings of the IEEE, vol. 79, No. 5, May 1982.

Dialog Search, May 18, 1994.

Caplus abstract of "The Misunobu reaction", David Hughes, Org. React. (n.Y.) (1992), 42, 335–656, Month Unknown.

Caplus abstract of "Transition metal–catalyzd cross–coupling reactions of unactivated C–X bonds", tien–Yau Luh, Rev. Heteroat. Chem. (1996), 15, 61–82, Month Unknown.

Caplus abstract of "An efficient synthesis of 3–substituted indoles by palladium–catalyzed coupling reaction of 3–tributylstannylindoles with organic triflates and halides", Ciattini et al., Tetrahedron Lett. (1994), 35(15), 2405–8, Month Unknown.

Caplus abstract of "Amino acids as the amine component in a Mannich reaction", Agabyan et al., USp. Khim. (1982), 51(4), 678–95, Month Unknown.

Caplus abstract of "The one–pot palladium catalyzed Witting reaction with allylic alcohols. Scope and limitations", Moreno–Manas et al., Synth. Commun. (1986), 16(9), 1003–13, Month Unknown.

Caplus abstract of "Application of intramolecular Heck reactions for forming congested quarternary carbon centers in complex molecule total synthesis", Larry Overman, Pure Appl. Chem. (1994), 66(7), 1723–30, Month Unknown.

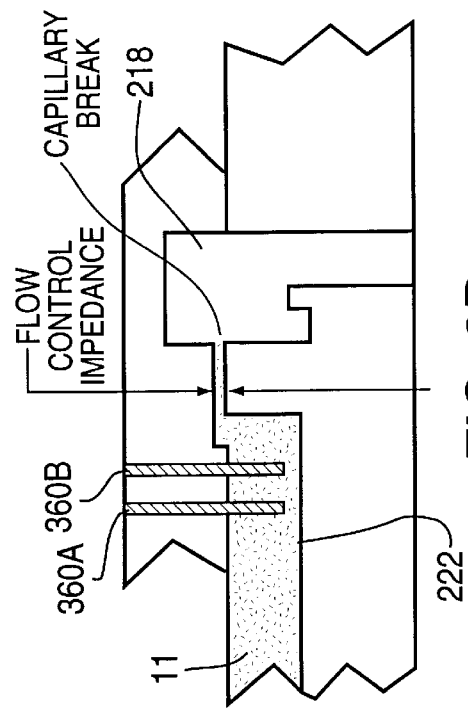
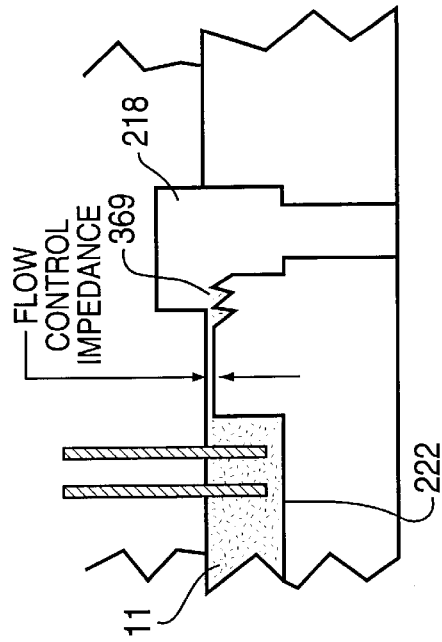
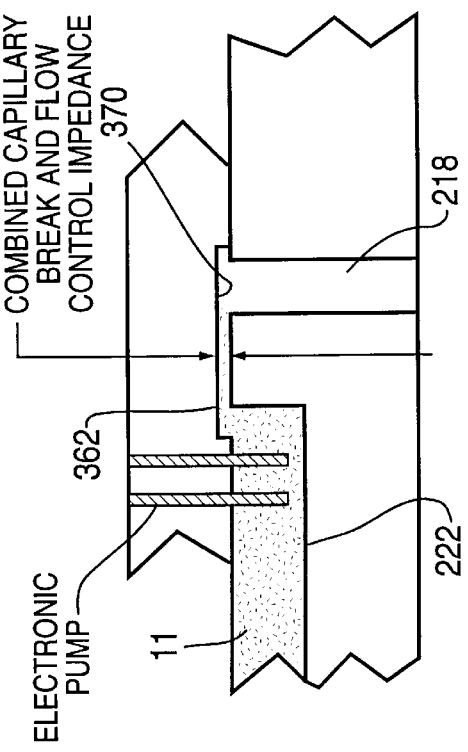
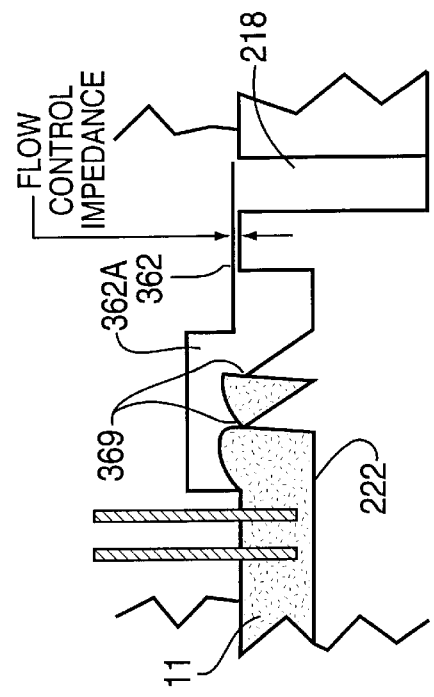

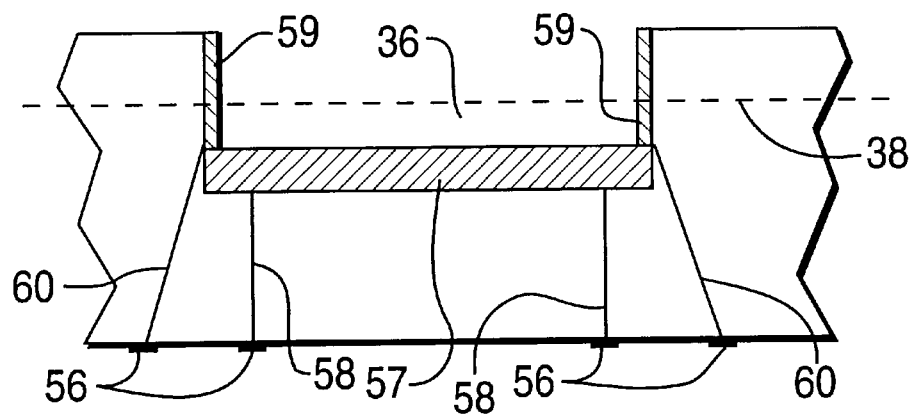
FIG. 14
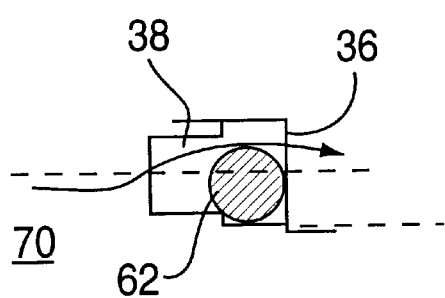 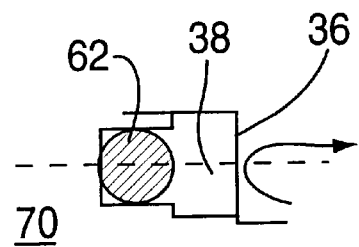
FIG. 15A  FIG. 15B

ELECTROKINETIC PUMPING

This application is a continuation-in-part of U.S. application Ser. No. 08/556,036 entitled "Liquid Distribution System," filed Nov. 9, 1995, now U.S. Pat. No. 5,846,396, which application is a continuation-in-part of U.S. application Ser. No. 08/338,703, titled "A Partitioned Microelectronic and Fluidic Device Array for Clinical Diagnostics and Chemical Synthesis," filed Nov. 10, 1994, now U.S. Pat. No. 5,545,069, a continuation-in-part of U.S. application Ser. No. 08/469,238, titled "Apparatus and Methods for Controlling Fluid Flow in Microchannels," filed Jun. 6, 1995, now U.S. Pat. No. 5,632,876, and a continuation-in-part of U.S. application Ser. No. 08/483,331, titled "Method and System for Inhibiting Cross-Contamination in Fluids of Combinatorial Chemistry Device," filed Jun. 7, 1995, now U.S. Pat. No. 5,603,351. This application is also and a continuation-in-part of U.S. application Ser. No. 08/556,423, titled "Electrokinetic Pumping," filed Nov. 9, 1995, now U.S. Pat. No. 5,858,193, which is a continuation-in-part of U.S. application Ser. No. 08/469,238, titled "Apparatus and Methods for Controlling Fluid Flow in Microchannels," filed Jun. 6, 1995, now U.S. Pat. No. 5,632,876, and a continuation-in-part of U.S. application Ser. No. 08/483,331, titled "Method and System for Inhibiting Cross-Contamination in Fluids of Combinatorial Chemistry Device," filed Jun. 7, 1995, now U.S. Pat. No. 5,603,351. All of the foregoing patent applications are hereby incorporated herein by reference in their entirety.

This application relates to electrode-based pumps, methods of operating such pumps, and calibration devices for such pumps.

Recently, a number of academic articles have focused on the problems associated with conducting chemical reactions on a micro-scale. This literature has discussed the possibility of managing such reactions on wafer-sized solid supports that have been etched to create microchannels. Reactor systems of this scale could allow multiple diagnostic or drug screening assays to be conducted in a transportable device that uses small amounts of reagents, thus reducing supply and disposal costs.

One mechanism for developing new drugs not provided for by nature has been dubbed "rational" drug design. This process looks at the structures of biological macromolecules as determined by crystallography and at the structures of pharmacological agents known to interact with these macromolecules. With the use of computer workstations, it was hoped that new pharmacological agents could be designed that had appropriately positioned functionalities for strongly interacting with the macromolecule. One difficulty with this approach is that growing crystals appropriate for crystallographic structural determinations is a tedious, empirical science. In many cases, it is unclear if appropriate crystals can be grown (for instance, for the glycoprotein hormones such a chorionic gonadotropin or other glycoproteins). Another difficulty is that chemistry does not provide the malleable construction tools evoked by the phrase "design"; instead, chemical building blocks provide only a limited number of bond angles and lengths. For example, the structural routes by which a chlorine group might be positioned in particular part of a drug-binding pocket in the macromolecule may be many, while the advantages or disadvantages of the ancillary structures needed to position this group are hard to "rationally" evaluate.

Combinatorial chemistry seeks to create its own "evolutionary" process that selects compounds with the desired pharmacological activity. The key to making the process evolutionary is to generate large families of "mutants", in this case families of compounds with some chemical relatedness but with clear differences. The concepts of rational design may be taken advantage of in selecting the families of compounds to be explored by the combinatorial method.

Combinatorial chemistry seeks to generate new leads to classes of compounds that have potential pharmacological activity. Traditionally, such leads have been found by screening various plant or animal extracts for pharmacological activity. Such extracts are tedious to obtain, may have very small concentrations of potentially useful compounds, and at best only contain compounds selected by evolutionary pressures that may have nothing to do with the disease that is sought to be treated. After an extract has been identified, the process provides little information as to the identity of the active ingredient.

Combinatorial chemistry seeks to create the large family of compounds by permutation of a relatively limited set of building block chemicals. Preferably, the combinatorial method will create identifiable pools containing one or more synthetic compounds. These pools need not be identifiable by the chemical structure of the component compounds, but should be identifiable by the chemical protocol that created the compounds. These pools are then screened in an assay that is believed to correlate with a pharmacological activity. Those pools that produce promising results are examined further to identify the component compounds and to identify which of the component compounds are responsible for the results.

The follow-up protocol used to identify the active compounds in a combinatorial pool can also involve a combinatorial method. For instance, the promising pool could result from the reaction, first, of a mixture of compounds A, B and C, which compounds do not react with one another, with compounds D, E and F, which compounds do not react with one another but do react with compounds A, B or C. Second, the resulting compounds are reacted with compounds G, H and I. To narrow the possible identity of the active compounds in the pool, the A-D, A-E, A-F, B-D, B-E, B-F, C-D, C-E and C-F products can be separately created by combinatorial chemistry and separately reacted with a the mixture of G, H and I. After this step, the sub-pool that is active in the screening assay generally will contain a more limited family of compounds.

Once promising molecules are identified by combinatorial chemistry, the identified molecules provide information that aides in the design of further combinatorial experiments. The full array of promising compounds identified by combinatorial chemistry can provide valuable information to guide traditional pharmaceutical chemistry efforts.

A popular tool in the emerging field of combinatorial chemistry is to attach the first chemical building blocks to a solid support, typically a glass or polymeric support, such as the supports used in the well known Merrifield method for synthesizing polypeptides. This attachment provides a mechanism for quickly isolating product by simply washing away reactants and related impurities and decoupling the product from the support. In some cases, the support-coupled product can be assayed for pharmacological activity.

Miniaturization is usefully employed in combinatorial chemistry since: (i) workers generally seek compounds that are pharmacologically active in small concentrations; (ii) in creating a vast "evolutionary" assortment of candidate molecules it is preferable to have the numerous reactions well documented and preferably under the direction of a limited number of workers to establish reproducibility of technique;

(iii) it is expensive to create a vast, traditionally-scaled synthetic chemistry complex for creating a sufficiently varied family of candidate compounds; and (iv) substantial concerns are raised by the prospect of conducting assays of the products of combinatorial chemistry at more standard reaction scales. Miniaturization allows for the economic use of robotic control, thereby furthering reproducibility.

The wafer-sized devices described above can be ideal for combinatorial chemistry, allowing for numerous synthetic chemistry reactions to be conducted substantially under computer control using only small quantities of reagents. However, the academic literature advocating such microscale devices has not adequately addressed fundamental issues in conducting combinatorial chemistry at this scale: for instance, how does one manage to effectively pump fluids in such a device to the multitude of microscaled reaction cells (e.g., 100 to 100,000) in the device? The present invention provides a pump that can be incorporated within such devices.

SUMMARY OF THE INVENTION

The invention provides methods of performing a synthetic process in a liquid distribution system having reaction cells, comprising pumping at least one reagent into a reaction cell. The synthetic processes include chemical reactions including, but are not limited to, a catabolic reaction, an anabolic reaction, an oxidation, a reduction, amide formation, a Mitsunobu reaction, Suzuki coupling, Stille coupling, alkylation of an amine, acylation of an amine, alkylation of a ketone, reductive amination, sulfonamide formation, DNA synthesis, cycloaddition, a Mannich reaction, a Diels Alder reaction, a Wittig reaction, a Heck reaction, elimination of a leaving group and a condensation reaction.

The synthetic processes also include the synthesis of a small molecule, a polymeric organic compound, an oligonucleotide or a peptide. The reagents in these synthetic processes include, but are not limited to, carboxylic acid, carbodiimide, sulfonamide, amine, alcohol, pyridine, azodicarboxylate, carbazole, azobenzene, amino N-oxide, 1,4-benzoquinone or ammonium perruthenate. In certain preferred embodiments, the synthetic process is carried out employing a solid support.

In certain preferred embodiments of the invention, particular reagents are pumped, preferably electrokinetically, into a reaction cell. For example, when the reaction is an oxidation, the reagents are preferably selected from the group consisting of m-chloroperbenzoic acids, hydrogen peroxide, and $KMnO_4$. When wherein the reaction is a reduction, the reagents are preferably selected from the group consisting of $LiAlH_4$ and lithium borohydride. When the reaction is amide formation, the reagents are preferably selected from the group consisting of o-benzotriazol-1-yl-N,N,N',N'-tetramethyluroniumhexafluorophosphate, 2,3-dichloro-5,6-dicyano-1,4-benzoquinonone, 1-hydroxybenzotriazole hydrate, protected amino acids, N-methyl morpholine and diisopropyl carbodiimide. When the reaction is a Mitsunobu reaction, the reagents are preferably selected from the group consisting of phenol, alcohol, diethylazodicarboxylate, triphenylphosphine and N-methyl morpholine. When the reaction is Suzuki coupling, the reagents are preferably selected from the group consisting of halide, paladium (0) catalyst, aryl boronic acid, triethyl amine and dimethyl formamide. When the reaction is Stille coupling, the reagents are preferably selected from the group consisting of halide, palladium (0) catalyst, aryl stannane, N-methyl pyrolidone and triphenyl arsine. When the reaction is alkylation or acylation of an amine, the reagents are preferably selected from the group consisting of tosylate, halide, amine, N-methyl pyrrolidone and phosgene. When the reaction is alkylation of a ketone, the reagents are preferably selected from the group consisting of amine, ketone, lithium diiosopropyl amine, tetrahydrofuran and alkyl iodide. When the reaction is reductive amination, the reagents are preferably selected from the group consisting of amine, aldehyde, sodium cyanoborohydride, sodium triacetyoxyborohydride, borohydrate pyridine and methylene chloride. When the reaction is sulfonamide formation, the reagents are preferably selected from the group consisting of amines, sulfonyl chloride and dimethylformamide. When the reaction is DNA synthesis, the reagents are preferably selected from the group consisting of oligonucleotides and phosphates. When the reaction is cycloaddition, the reagents are preferably selected from the group consisting of peracids, substituted alkenes, diazo compounds, azide, nitriles, azomethine ylide, nitrones and carbonyl oxides. When the reaction is a Mannich reaction, the reagents are preferably selected from the group consisting of aldehydes, ketones, amine salts, amides, acids and bases. When the reaction is a Diels Alder reaction, the reagents are preferably selected from the group consisting of substituted alkenes and dienes. When the reaction is a Wittig reaction, the reagents are selected from the group consisting of triphenylphosphines and substituted alkenes. When the reaction is a Heck reaction, the reagents are preferably selected from the group consisting of a palladium (0) catalyst, substituted alkenes, substituted halides and triethylamines. When the reaction is elimination of a leaving group, the reagents are preferably selected from the group consisting of alkyl halides and bases.

BRIEF DESCRIPTION OF THE DRAWINGS

FIGS. 9A–9D show various capillary barrier designs.

FIG. 14 shows a reaction cell having a heater and a thermocouple.

FIGS. 15A and 15B show a valve design.

DEFINITIONS

Figure 1:
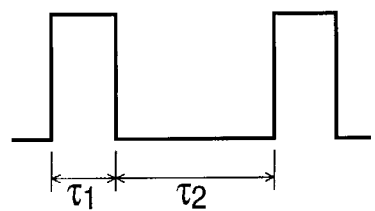
FIG. 1 shows a voltage pulse pattern used to power an electrode-based pump useful in the liquid distribution system.

The following terms shall have the meaning set forth below:

addressable
: a reaction cell or channel is "addressable" by a reservoir or another channel if liquid from the reservoir or other channel can be directed to the reaction cell or channel.

adjacent
: "adjacent" as used in these situations: (i) a first structure in one of the plates is adjacent to a second structure in the same or another plate if the vertical projection of the first structure onto the plate of the second structure superimposes the first structure on the second or places it within about 250 pm of the second; and (ii) groupings of two or more channels are adjacent to one another if each channel is in substantially the same horizontal plane, and all but the outside two channels in the grouping are adjacent (in the sense defined in (i) above) to two neighbor channels in the grouping. Preferably, under item (i), a first structure is adjacent to a second structure if the vertical projection of the first structure onto the plate of the second structure superimposes the first structure on the second or places it within about 150 $\mu$m of the second.

capillary dimensions
: dimensions that favor capillary flow of a liquid. Typically, channels of capillary dimensions are no wider than about 1.5 mm. Preferably channels are no wider than about 500 $\mu$m, yet more preferably no wider than about 250 $\mu$m, still more preferably no wider than about 150 $\mu$m.

capillary barrier
: a barrier to fluid flow in a channel comprising an opening of the channel into a larger space designed to favor the formation, by liquid in the channel, of an energy minimizing liquid surface such as a meniscus at the opening. Preferably, capillary barriers include a dam that raises the vertical height of the channel immediately before the opening into the larger space.

connected
: the channels, reservoirs and reaction cells of the invention are "connected" if there is a route allowing fluid between them, which route does not involve using a reaction cell as part of the link.

directly connected
: reservoirs and horizontal channels are "directly connected" if they are connected and either (1) no other channel is interposed between them or (2) only a single vertical channel is interposed between them.

flow preference
: the direction that a liquid pumps under the influence of an electrode-based pump having two symmetrically situated rod-shaped electrodes.

hole diameter
: because techniques for fabricating small holes often create holes that are wider at one end than the other (for instance, about 50 microns wider), the hole diameter values recited to herein refer to the narrowest diameter.

horizontal, vertical, EW, NS
: indications of the orientation of a part of the distribution system refer to the orientation when the device is in use. The notations "EW axis" and "NS axis" are in reference to FIGS. 1, 2, 3 and 7, where an EW axis goes from right to left and is perpendicular to the long axis of the page and a NS axis is from top to bottom parallel to the long axis of the page.

independent
: channels, reservoirs or reaction cells that are not connected.

offset
: two sets of channels are "offset" when none of the channels in the first such set is adjacent to any of the channels in the second set.

perpendicular
: channels in the distribution plate are perpendicular even if primarily located on separate horizontal planes if their vertical projections onto the same horizontal plane are perpendicular.

reservoir
: unless a different meaning is apparent from the context, the terms "reservoir" and "fluid reservoir" include the horizontal extension channels (sometimes simply termed "extensions") directly connected to the reservoir or fluid reservoir.

second reservoir extension channels
: these extension channels include the distribution channels that may branch off of these extension channels.

substantially the length of one of the horizontal dimensions
: at least about 70% of one of the major horizontal dimensions (e.g. the EW or NS dimensions illustrated in the Figures) of the distribution plate.

U-plumbing channel
: a channel designed to connect at least two channels or reservoirs such that the liquid level in one of the connected channels or reservoirs will equalize with the liquid level in the other connected channel or reservoirs due to hydrological forces. U-plumbing channels typically have vertical channels that connect channels or reservoirs located in a higher vertical plane with a substantially horizontal channel segment of the U-plumbing channel located in a lower plane—these vertical and horizontal segments together comprise the U-plumbing channel. The feeder channels of the invention are typically U-plumbing channels.

DETAILED DESCRIPTION

The invention provides methods of performing a synthetic process, such as a chemical reaction, in a liquid distribution system having reaction cells, comprising pumping at least one reagent into a reaction cell. A "reagent" is defined herein as a substance used in a chemical reaction. Reagents include, but are not limited to, solvents, catalysts and reactants. Any chemical reaction with reaction conditions suitable for the hydrologic liquid distribution system can be used in the methods of the present invention, including the chemical reactions cited in March, *Advanced Organic Chemistry Reactions, Mechanisms and Structure* (John Wiley & Sons, 1992), which is hereby incorporated by reference in its entirety. The chemical reactions include, but are not limited to, a catabolic reaction, an anabolic reaction, an oxidation, a reduction, amide formation, a Mitsunobu reaction, Suzuki coupling, Stille coupling, alkylation of an amine, acylation of an amine, alkylation of a ketone, reductive amination, sulfonamide formation, DNA synthesis, cycloaddition, a Mannich reaction, a Diels Alder reaction, a Wittig reaction, a Heck reaction, elimination of a leaving group and a condensation reaction.

The following publications, all of which are incorporated by reference herein in their entirety, provide a description of chemical reactions for use in methods of the present inventions. For a description of amide formation, see, for example, *Tet. Lett.* 30:1827 (1989), *Tet Lett.* 30:4645 (1989), *Syn. Comm.* 23:349 (1993) and *J. Org. Chem.* 44:5000 (1979). For a description of a Mitsunobu reaction, see, for example, *Tet Lett.* 35:4705 (1994). For a description of Suzuki coupling, see, for example, *Tet Lett.* 49:9177 (1994). For a description of Stille coupling, see, for example, *Tet Lett.* 35:5613 (1994) and *J. Org. Chem.* 60:523 (1995). For a description of alkylation of an amine, see, for example, *J. Org. Chem.* 38:1427 (1995). For a description of acylation of an amine, see, for example, *Ang. Chem. Int. Ed.* 34:907 (1995). For a description of alkylation of a ketone, see, for example, *Ang. Chem. Int. Ed.* 18:221 (1979). For a description of reductive amination, see, for example, *J. Am. Chem. Soc.* 93:2897 (1971), *Synthesis* 135 (1075) and *Tet Lett.* 31:5547 (1990). For a description of sulfonamide formation, see, for example, *J. Org. Chem.* 38:1427 (1995). For a description of cycloaddition reactions, see, for example, *Advanced Organic Chemistry, Part B, "Reactions and Synthesis"* (Plenum Press, NY 1983). For a description of a Mannich reaction, see, for example, *Tetrahedron* 46:1791 (1990) and *Synthesis* 703 (1973). For a description of a Diels Alder reaction, see, for example, *Diels Alder Reactions* (Elsevier, N.Y. 1965). For a description of a Wittig reaction, see, for example, *Org. React.* 25:73 (1977) and *Chem. Rev.* 74:87 (1974). For a description of an oxidation reaction, see, for example, *Oxidations in Organic Chemistry, Part C* (Academic Press, NY 1978) at page 211. For a description of elimination of a leaving group, see, for example, *The Chemistry of Functional Groups Supplement D, Part 2* (Wiley, NY 1983), at page 1173.

The synthetic processes also include the synthesis of a small molecule, a polymeric organic compound, an oligonucleotide or a peptide. The reagents in these synthetic processes include, but are not limited to, carboxylic acid, carbodiimide, sulfonamide, amine, alcohol, pyridine, azodicarboxylate, carbazole, azobenzene, amino N-oxide, 1,4-benzoquinone or ammonium perruthenate. In certain preferred embodiments, the synthetic process is carried out employing a solid support.

In certain preferred embodiments of the invention, particular reagents are electrokinetically pumped into a reaction cell. For example, when the reaction is an oxidation, the reagents are preferably selected from the group consisting of m-chloroperbenzoic acids, hydrogen peroxide, and $KMnO_4$. When wherein the reaction is a reduction, the reagents are preferably selected from the group consisting of $LiAlH_4$ and lithium borohydride. When the reaction is amide formation, the reagents are preferably selected from the group consisting of o-benzotriazol-1-yl-N,N,N',N'-tetramethyluroniumhexafluorophosphate, 2,3-dichloro-5,6-dicyano- 1,4-benzoquinonone, 1-hydroxybenzotriazole hydrate, protected amino acids, N-methyl morpholine and diisopropyl carboiimide. When the reaction is a Mitsunobu reaction, the reagents are preferably selected from the group consisting of phenol, alcohol, diethylazodicarboxylate, triphenylphosphine and N-methyl morpholine. When the reaction is Suzuki coupling, the reagents are preferably selected from the group consisting of halide, palladium (0) catalyst, aryl boronic acid, triethyl amine and dimethyl formamide. When the reaction is Stille coupling, the reagents are preferably selected from the group consisting of halide, paldium (0) catalyst, aryl stannane, N-methyl pyrolidone and triphenyl arsine. When the reaction is alkylation or acylation of an amine, the reagents are preferably selected from the group consisting of tosylate, halide, amine, N-methyl pyrolidone and phosgene. When the reaction is alkylation of a ketone, the reagents are preferably selected from the group consisting of amine, ketone, lithium diiosopropyl amine, tetrahydrofuran and alkyl iodide. When the reaction is reductive amination, the reagents are preferably selected from the group consisting of amine, aldehyde, sodium cyanoborohydride, sodium triacetyoxyborohydride, borohydrate pyridine and methylene chloride. When the reaction is sulfonamide formation, the reagents are preferably selected from the group consisting of amines, sulfonyl chloride and dimethylformamide. When the reaction is DNA synthesis, the reagents are preferably selected from the group consisting of oligonucleotides and phosphates. When the reaction is cycloaddition, the reagents are preferably selected from the group consisting of peracids, substituted alkenes, diazo compounds, azide, nitriles, azomethine ylide, nitrones and carbonyl oxides. When the reaction is a Mannich reaction, the reagents are preferably selected from the group consisting of aldehydes, ketones, amine salts, amides, acids and bases. When the reaction is a Diels Alder reaction, the reagents are preferably selected from the group consisting of substituted alkenes and dienes. When the reaction is a Wittig reaction, the reagents are selected from the group consisting of triphenylphosphines and substituted alkenes. When the reaction is a Heck reaction, the reagents are preferably selected from the group consisting of a palladium (0) catalyst, substituted alkenes, substituted halides and triethylamines. When the reaction is elimination of a leaving group, the reagents are preferably selected from the group consisting of alkyl halides and bases.

A. Electrode-based Pumps

At least two types of such electrode-based pumping has been described, typically under the names "electrohydrodynamic pumping" (EHD) and "electroosmosis" (EO). EHD pumping has been described by Bart et al., "Microfabricated Electrohydrodynamic Pumps," *Sensors and Actuators*, A21–A23: 193–197, 1990 and Richter et al., "A Micromachined Electrohydrodynamic Pump," *Sensors and Actuators*, A29:159–168, 1991. EO pumps have been described by Dasgupta et al., "Electroosmosis: A Reliable Fluid Propulsion System for Flow Injection Analysis," *Anal. Chem.*, 66: 1792–1798, 1994. In the present application, pumping effected with electrodes is termed "electrokinetic pumping."

EO pumping is believed to take advantage of the principle that the surfaces of many solids, including quartz, glass and the like, become charged, negatively or positively, in the presence of ionic materials, such as salts, acids or bases. The charged surfaces will attract oppositely charged counter ions in solutions of suitable conductivity. The application of a voltage to such a solution results in a migration of the counter ions to the oppositely charged electrode, and moves the bulk of the fluid as well. The volume flow rate is proportional to the current, and the volume flow generated in the fluid is also proportional to the applied voltage. Typically, in channels of capillary dimensions, the electrodes effecting flow can be spaced further apart than in EHD pumping, since the electrodes are only involved in applying force, and not, as in EHD, in creating charges on which the force will act. EO pumping is generally perceived as a method appropriate for pumping conductive solutions.

EHD pumps have typically been viewed as suitable for moving fluids of extremely low conductivity, e.g., $10^{-14}$ to $10^{-9}$ S/cm. It has now been demonstrated herein that a broad range of solvents and solutions can be pumped using appropriate solutes than facilitate pumping, using appropriate electrode spacings and geometries, or using appropriate pulsed or d.c. voltages to power the electrodes, as described further below.

The electrodes of first pumps 360 and second pumps 361 used in the liquid distribution system described below preferably have a diameter from about 25 microns to about 100 microns, more preferably from about 50 microns to about 75 microns. Preferably, the electrodes protrude from the top of a channel to a depth of from about 5% to about 95% of the depth of the channel, more preferably from about 25% to about 50% of the depth of the channel. Usually, as a result the electrodes, defined as the elements that interact with fluid, are from about 5 microns to about 95 microns in length, preferably from about 25 microns about to 50 microns. Preferably, a pump includes an alpha electrode 364 (such as first electrode 360A or third electrode 361A) and a beta electrode 365 (such as third electrode 360B and fourth electrode 361B) that are preferably spaced from about 100 microns to about 2,500 microns apart, more preferably, from about 1 50 microns to about 1000 microns apart, yet more preferably from about 250 microns to about 1000 microns apart, or, in an alternate embodiment, from about 150 microns to about 250 microns apart. The separation of electrodes shall be measured from the center points of the electrodes as they first protrude into their associated fluid channel. In a particularly preferred embodiment, a gamma electrode 366 (not shown) is spaced from about 200 microns to about 5,000 microns, more preferably from about 500 microns to about 1,500 microns, yet more preferably about 1,000 microns from the farther of the alpha electrode 364 and the beta electrode 365. In an alternative preferred embodiment, the pump has two additional electrodes comprising a gamma electrode 366 (not shown) and a delta electrode 367 that are spaced from about 200 microns to about 5,000 microns, more preferably from about 500 microns to about 1,500 microns, yet more preferably about 1,000 microns apart. Where the electrodes are located in fluid channels that have bends, the distances are measured along a line that defines the center line of the fluid channel. In contexts where relatively low conductivity fluids are pumped, voltages are applied across the alpha electrode 364 and the beta electrode 365, while in contexts where relatively more highly conductive fluids are pumped the voltage is induced between gamma electrode 366 and one of alpha electrode 364, beta electrode 365 or delta electrode 367. The latter circumstance typically applies for solvents traditionally pumped with EO pumping, although this invention is not limited to any theory that has developed around the concepts of EHD or EO pumping. No firm rules dictate which electrode combination is appropriate for a given solvent or solution; instead an appropriate combination can be determined empirically in light of the disclosures herein.

The voltages used across alpha and beta electrodes 364 and 365 when the pump is operated in d.c. mode are typically from about 40 V to about 2,000 V, preferably from about 50 to about 1,500V, more preferably ably from about 100 V to about 750 V, yet more preferably from about 200 V to about 300 V. The voltages used across gamma electrode 366 and alpha, beta or delta electrodes 364, 365 or 367 when the pump is operated in d.c. mode are typically from about 40 V to about 2,000 V, preferably from about 50 to about 1,500V, more preferably ably from about 100 V to about 750 V, yet more preferably from about 200 V to about 300 V. The voltages used across alpha and beta electrodes 364 and 365 when the pump is perated in pulsed mode can be as indicated above for d.c. mode, but are typically from about 50 V to about 1,000 V, preferably from about 100 V and about 400 V, more preferably from about 200 V to about 300 V. The voltages used across gamma electrode 366 and the alpha, beta or gamma electrode 364, 365 or 367 when the pump is operated in pulsed mode can be as indicated above for d.c. mode, but are typically from about 50 V to about 1,000 V, preferably from about 100 V and about 400 V, more preferably from about 200 V to about 300 V. Preferably, the ratio of pumping to current will be such that no more than about one electron flows into the solution adjacent to a first pump 360 or second pump 361 for every 1,000 molecules that move past the pump 360 or 361, more preferably for every 10,000 molecules that move past the pump 360 or 361, yet more preferably for every 100,000 molecules that move past the pump 360 or 361.

It is believed that an electrode-based internal pumping system can best be integrated into the liquid distribution system of the invention with flow-rate control at multiple pump sites and with relatively less complex electronics if the pumps are operated by applying pulsed voltages across the electrodes. FIG. 1 shows an example of a pulse protocol where the pulse-width of the voltage is $T_1$ and the pulse interval is $T_2$. Typically, $T_1$ is between about 1 μs and about 1 ms, preferably between about 0.1 ms and about 1 ms. Typically, $T_2$ is between about 0.1 μs and about 10 ms, preferably between about 1 ms and about 10 ms. A pulsed voltage protocol is believed to confer other advantages including ease of integration into high density electronics (allowing for hundreds of thousands of pumps to be embedded on a wafer-sized device), reductions in the amount of electrolysis that occurs at the electrodes, reductions in thermal convection near the electrodes, and the ability to use simpler drivers. The pulse protocol can also use pulse wave geometries that are more complex than the block pattern illustrated in FIG. 1.

Another, procedure that can be applied is to use a number of electrodes, typically evenly spaced, and to use a travelling wave protocol that induces a voltage at each pair of adjacent electrodes in a timed manner that first begins to apply voltage to the first and second electrodes, then to the second and third electrodes, and so on. Such methods are described in Fuhr et al., *J. Microelectrical Systems,* 1: 141–145, 1992. It is believed that travelling wave protocols can induce temperature gradients and corresponding conductivity gradients that facilitate electric field-induced fluid flow. Such temperature gradients can also be induced by positioning electrical heaters in association with the electrode-based first pumps 360 and second pumps 361.

While not wishing to be restricted to theory, several theoretical concepts are believed to play a role in the mechanics of EHD pumping. The forces acting on a dielectric fluid are believed to be described by:

$$\overline{F} = q\overline{E} + \overline{P} \cdot \nabla \overline{E} - \frac{1}{2}E^2 \nabla \varepsilon + \nabla \left[ \frac{1}{2} \rho \frac{\partial e}{\partial \rho} E^2 \right]$$

where F is the force density, q is the charge density, E is the applied field, P is the polarization vector, $\epsilon$ is the permittivity and $\rho$ is the mass density. Of the terms in the equation, the first and third are believed to be the most significant in the context of EHD pumping of fluids. The first term (qE) relates to the Coulomb interaction with a space-charge region. The third term ($½E^2\nabla\epsilon$) relates to the dielectric force which is proportional to the gradient in permittivity.

In low fields, i.e., the Ohmic region where current is linearly proportional to voltage, the primary source of charges that will be acted upon by the electric field are believed to be primarily due to ions from additives, ions from impurities and ions formed by autodissociation of molecules in the fluid. In intermediate fields, i.e. from beyond the Ohmic region to about 2 V/μm, the charges are believed to be primarily formed by dissociation and electrolylytic processes in the fluid. In higher fields, the charges are believed to be determined by injection processes at the electrodes, which electrodes inject homocharges.

For the purposes of this application, positive (+) flow shall be flow in the direction of the negative electrode, and negative (−) flow shall be flow in the direction of the positive electrode.

In a preferred embodiment of the invention, the controller 10 has a device for storing data and stores the values of voltage and polarity suitable for pumping a number of solvents.

Experimental results indicate that the properties of fluid flow (like direction of flow) correlate well with the solvent's ability to stabilize and solvate the charged species injected or induced from the electrodes. The direction of flow is believed to be determined by the preference of the solvent to solvate either cations or anions. This salvation preference is believed to imply a greater shell of solvent molecules that will be dragged in an electric field, creating fluid movement, when a field is applied to the electrodes of a first pump 360 or a second pump 361. For example, a preferred solvation of cations correlates with a preference for fluid flow from the anode to the cathode (i.e., the positive direction). The degree of such a salvation preference for a solvent is believed to depend on the ability of the molecules within the solvent to accept or donate hydrogen bonds. In one aspect of the invention, for liquids whose pumping behavior has not yet been characterized, the controller will store initial pumping parameters estimated using on the Linear Solvation Energy relationships established by R. W. Taft and co-workers. See, Kamlet et al., *J. Org. Chem.*, 48: 2877–2887, 1983 and Kamlet et al., *Prog. Phys. Org. Chem.*, 13: 485, 1981. These workers have categorized solvents in terms of the following parameters: $\pi$, the ability of the solvent to stabilize a stabilize a charge or dipole by virtue of its dielectic properties; $\alpha$, the hydrogen bond donating ability of the solvent; and $\beta$, the hydrogen bond accepting ability of the solvent. These parameters are more fully defined in the above-cited Kamlet et al. publications, from which these definitions are incorporated herein by reference.

Using a one mm capillary of circular cross-section, a pair of 50 micron rod-shaped, platinum electrodes perpendicularly inserted to a depth of 500 microns into the capillary with a 500 micron separation powered by a 400 V field, the direction of flow was determined for several solvents. The direction of flow and the $\alpha$, $\beta$, $\pi$, $\epsilon$ and dipole moment values are as follows:

| Solvent | direction | α | β | π | ε | dipole moment |
|---|---|---|---|---|---|---|
| ethanol | − | 0.83 | 0.77 | .54 | 24.55 | 1.69 |
| tetrahydrofuran | + | 0 | 0.55 | .58 | 7.58 | 1.75 |
| chloroform | − | 0.44 | 0 | .58 | 4.806 | 1.01 |
| acetone | + | 0.08 | 0.48 | .71 | 20.7 | 2.69 |
| methanol | − | 0.93 | 0.62 | .6 | 32.7 | 2.87 |
| 2-propanol | +/− | 0.76 | 0.95 | .48 | 19.92 | 1.66 |
| acetonitrile | + | 0.19 | 0.31 | .75 | 37.5 | 3.92 |
| N-methyl-pyrrolidone | + | 0 | 0.77 | .92 | 32.0 | 4.09 |
| diethyl ether | + | 0 | 0.47 | 0.27 | 4.335 | 1.15 |
| 1,2 dichloro ethane | − | 0 | 0 | 0.81 | 10.36 | 1.2 |
| DMF | + | 0 | 0.69 | .88 | 36.71 | 3.86 |

It is believed that the $\alpha$ and $\beta$ values reflect the ability of the solvent under an electric field to solvate a negative or positive charged species, with the magnitude of $\alpha-\beta$ correlating with (−) flow, and the magnitude of $\beta-\alpha$ correlating with (+) flow. According to one aspect of the invention, the preferred direction of flow of a liquid can be reversed from that predicted as above if the fluid has a difference in $\alpha$ and $\beta$ values that is small but not zero and the electrode pair used creates an asymmetric field, such that the acting force on either positive or negative charged species is enhanced. One such electrode pair has an alpha electrode 364 with that points in the direction of intended flow and a beta electrode 365 that lines the walls of the channel in which it is located. Preferably, the alpha electrode 364 sufficiently points in the direction of flow such that its point defines a line that intersects the plane defined by the beta electrode 365. Preferably, the alpha electrode 364 ends in a point or wedge shape. Such an electrode-based pump, fabricated in a 1 mm capillary, has been shown to be effective to pump 2-propanol in the direction pointed to by the alpha electrode 364 either when the voltage applied to the electrodes implied a (−) direction of flow or, with somewhat weaker flow, when the voltage applied to the electrodes implied a (+) direction of flow.

Figure 2A:
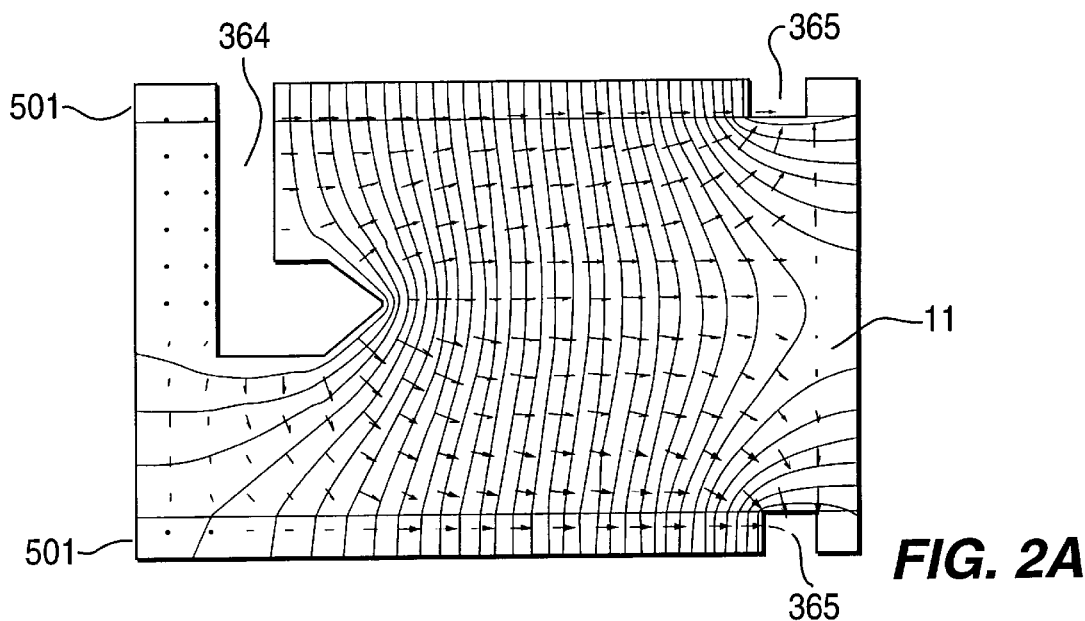
FIGS. 2A and 2B show the field strength and orientation at numerous points about electrode-based pumps.

The asymmetric, electrode-based pump effective to pump 2-propanol in the direction pointed to by the alpha electrode 364 is illustrated in FIG. 2A. Alpha electrode 364 points from left to right in the figure. Beta electrode 365 is a ring electrode that is flush with the sides of the capillary 501. Using the QuickField program available from Tera Analysis, Granada Hills, Calif., the electric field strengths and orientations at various points about the electrodes is indicated by the size and orientation of the arrow at that point. It can be seen from FIG. 2A that where alpha electrode 364 acts as a cathode, the area where a solvated negative ion would be influenced by a strong field pushing it in the (+) direction is greater than the area where a strong field would push a solvated positive ion in the (−) direction. The integration of these forces acting on these solvation spheres explains why asymmetric fields can be used to pump a liquid against its ordinary preferred direction of flow. Thus, depending on the liquids to be pumped, asymmetric fields can be used to assure a given direction of flow.

Figure 2B:
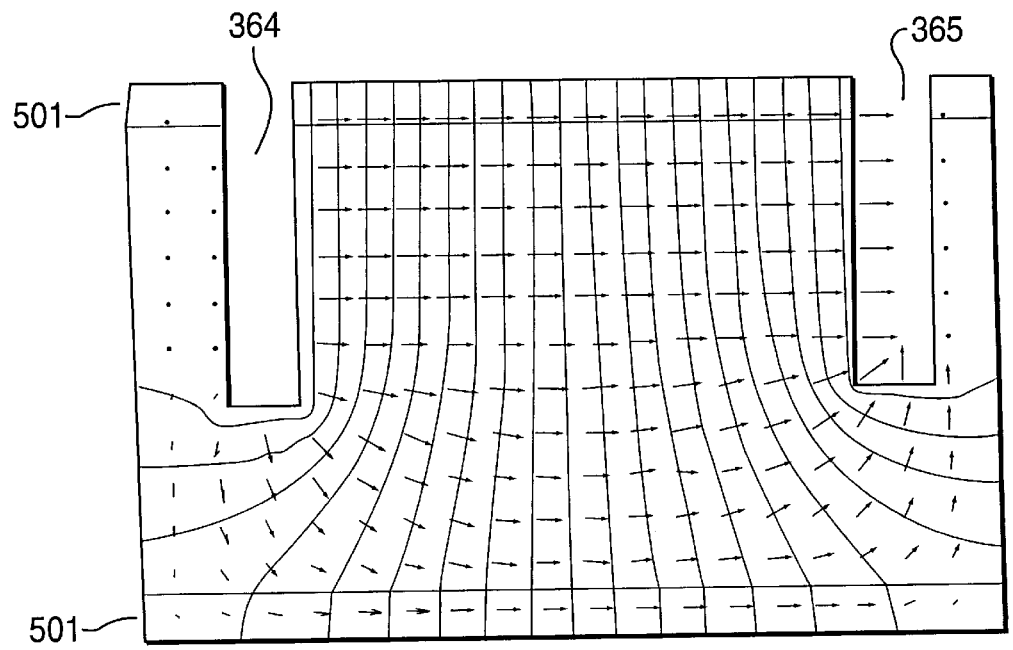

For comparison purposes, FIG. 2B shows the field strength and orientation of a number of points about a more symmetrical pump having alpha electrode 364 and beta electrode 365.

The pumping parameters of a liquid can be calibrated using a plug of the liquid disposed in a capillary that has an electrode-based pump and is angled uphill. If optical devices are associated with the capillary for monitoring the position of the plug, the velocity of pumped flow uphill and the velocity of gravity driven downhill motion can be measured. With these velocities and the angle of the capillary, the pressure applied to the liquid can calculated. (Fluid resistance, $R=(8\cdot\mu\cdot l)/\pi r^4$, where $\mu$ defines viscosity and l=the length of the fluid plug; Pressure, $P=RA(v_{up}-v_{down})$, where A=cross-sectional area). The efficiency of the pump can also be calculated ($\eta=(q\cdot\rho\cdot Q\cdot N_A)/m\cdot l$, where q=charge of $e^-$, $\rho$=density of liquid, $Q$=flow rate=$v_{up}\cdot A$, m=mass of liquid, and I=current). The velocities can be measured with multiple single point observations of the location of either the front or rear interfaces of the plug using fixed LEDs and optical detectors or in a continuous mode using a light and a silicon photodiode position sensor, such as a SL15 or SC10 position sensor available from UDT Sensors, Inc., Hawthorne, Calif. With the latter method, the correlation between the signal produced at the difference amplifier connected to the position sensor must be calibrated prior to experimental use.

Figure 3:
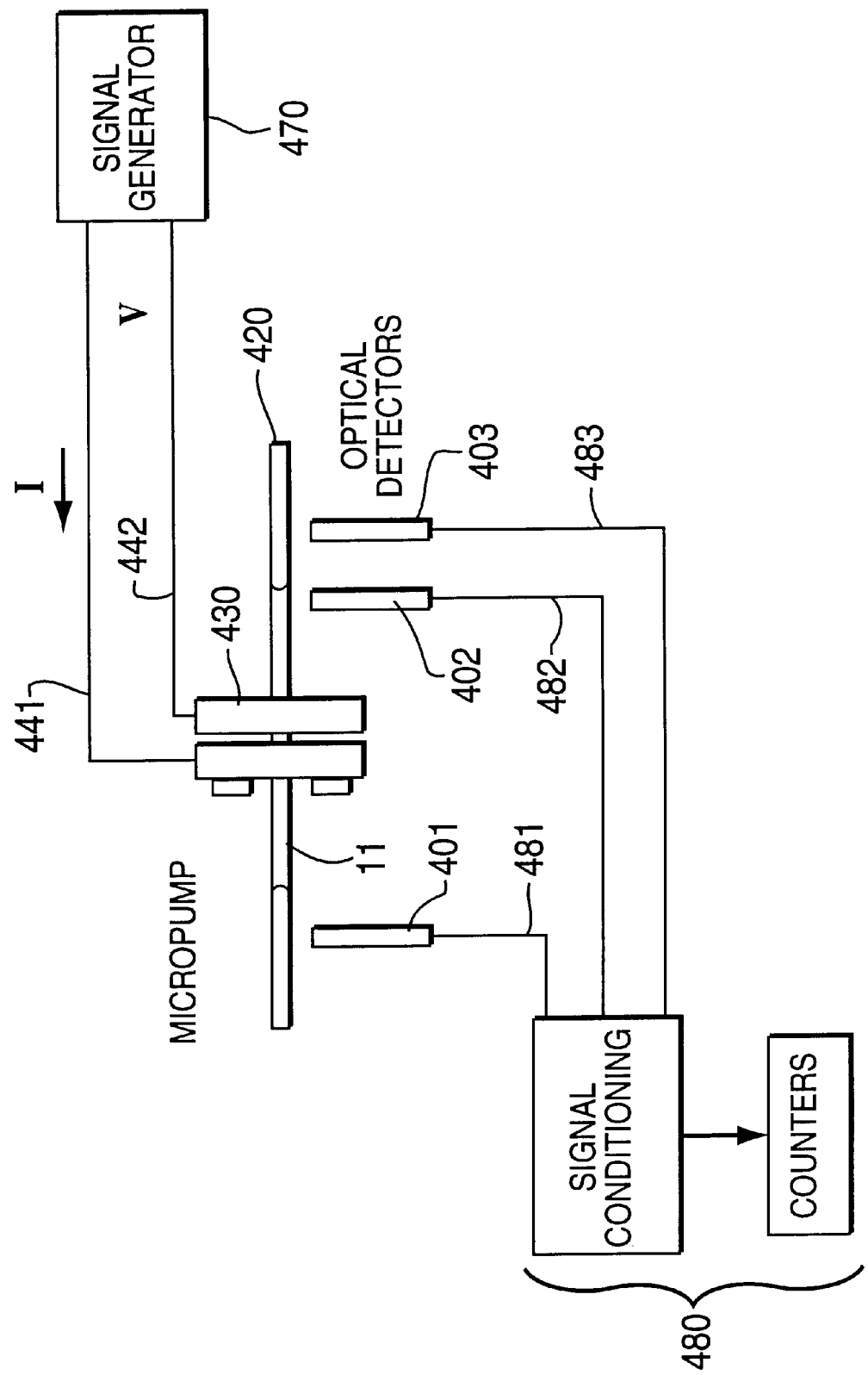
FIG. 3 shows a calibration device.

FIG. 3 shows a calibration device having first optical detector 401, second optical detector 402 and third optical detector 403. These are preferably photodiodes such as the OTS-254 phototransister available from Opto Technnology, Inc., Wheeling, Ill. Not shown are corresponding first light source 411, second light source 412 and third light source 413. These are preferably LEDs such as the Super Bright LEDs available from Radio Shack. A capillary 420 is situated in mount 430. Mount 430 can be manipulated to orient capillary 420 at an angle offset from a horizontal orientation. First lead 441 and second lead 442 relay voltage to the electrode based pump 460 (obscured by mount 430) from the voltage-generating portion 470 of controller 10. Electrical signals correlating with light detection are relayed to the signal processing portion 480 of controller 10 by way of first data lead 481, second data lead 482 and third data lead 483. In operation, the signals from first optical detector 401, second optical detector 402 and third optical detector 403 will show a transition point when the interface of a plug 11 of liquid in capillary 420 goes by the respective detector (401, 402 or 403). The timing of these transitions provides a measure of the velocity of movement of the plug 11.

Figure 4:
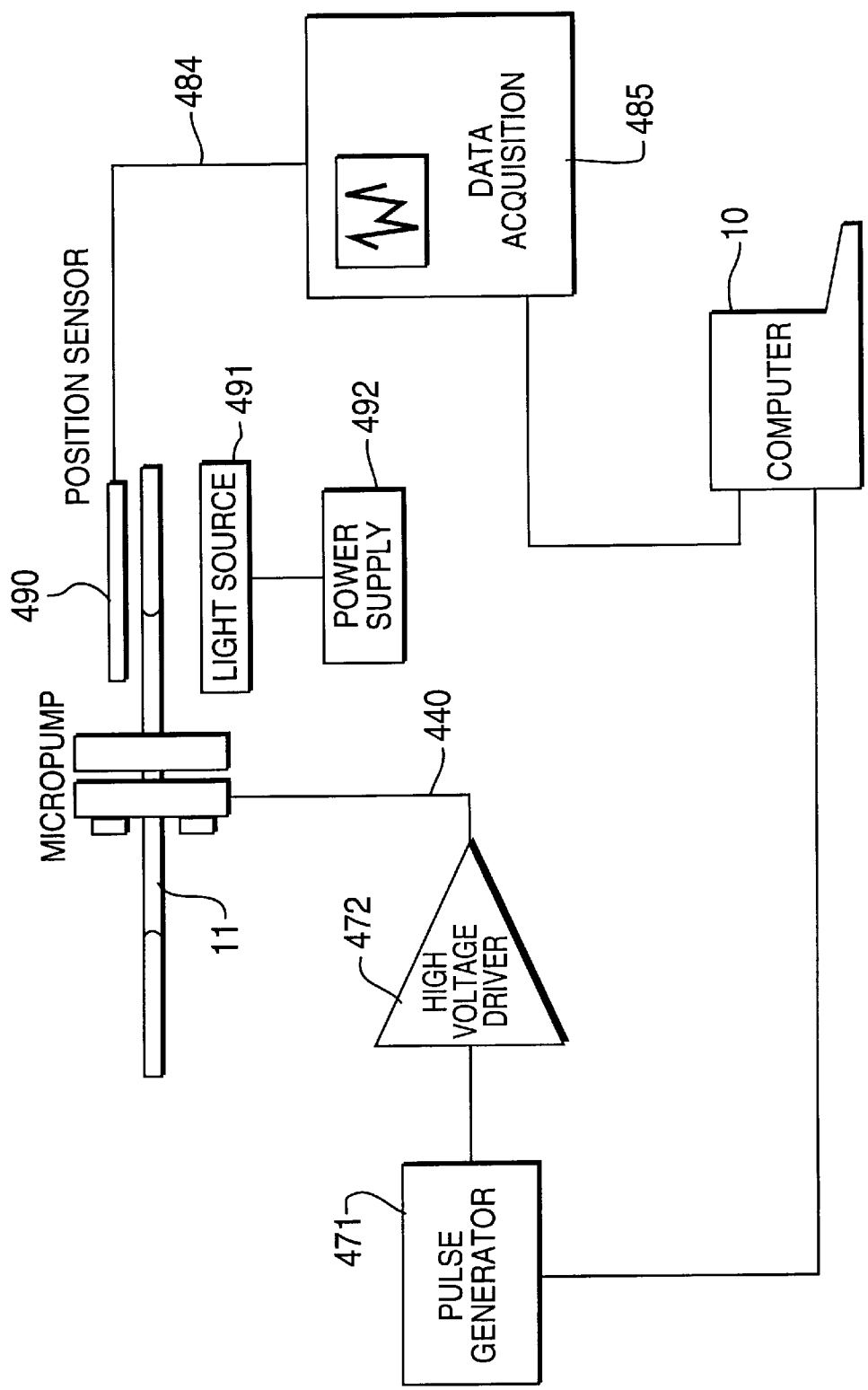
FIG. 4 shows another calibration device.

FIG. 4 shows a calibration device having a position sensor 490 which generates electrical signals based on the distribution of light from light source 491 that impacts the surface of the position sensor 490. Light source 491 has a power source 492. Leads 440 that relay voltage to pump 460 are shown schematically. The voltage is controlled by the controller 10 through its pulse generator 471 and voltage driver 472. Electrical output from the position sensor is relayed via leads 484 to the data acquisition module 485 of controller 10. It will be recognized that the signal from the position sensor can be calibrated so that it can be processed to determine the position of the interface of plug 11. This information can be used to calculated the velocity of the movement of plug 11.

The pumping parameters for a number of solvents have been determined in the 1 mm capillary described above, as follows:

| Solvent | Flow rate, Q $\mu$l/sec | Pressure, P $N/m^2$ | electrical efficiency, $\eta$, molecules/$e^-$ |
|---|---|---|---|
| acetone | 14.56 | 16.33 | $1.9 \times 10^6$ |
| methanol | 24.46 | 26.32 | $9.7 \times 10^4$ |
| 1-propanol | 16.39 | 74.89 | $4.2 \times 10^5$ |
| diethyl ether | 18.44 | 20.45 | $5.8 \times 10^8$ |
| 1,2 dichloroethane | 14.24 | 46.55 | $2.9 \times 10^7$ |

Another aspect of pumping is the observation that fluids that are resistant to pumping at a reasonable field strength can be made more susceptible to electrode-based pumping by adding a suitable pumping additive. Preferably, the pumping additive is miscible with the resistant fluid and can be pumped at high pressure, P, high flow rate, Q, and good electrical efficiency, $\eta$ (i.e., molecules pumped per electron of current). Generally, the pumping additive comprises from about 0.05 % w/w to about 10 % w/w of the resulting mixture, preferably from about 0.1% w/w to about 5% w/w, more preferably from about 0.1% w/w to about 1% w/w. Carbon tetrachloride and cyclohexane do not pump using the electrode pump situated in a capillary described above at a voltage of 2,000 V. By adding 0.5% w/w acetone or methanol as a pumping additive, both of these fluids can be pumped at a voltage of 1,000 V. In some cases, it is desirable to reverse the preferred flow direction of a liquid by mixing with it a pumping additive that strongly pumps in the desired direction. In all cases, pumping additives are selected on the basis of their pumping characteristics and their compatibility with the chemistries or other processes sought to be achieved in the liquid distribution system.

The electrode-based pumps of the invention can be operated to as a valve to resist flow in a certain direction by operating the pumps to counter the unwanted flow. To power the electrode-based pumps, one or more digital drivers, consisting of, for example, a shift register, latch, gate and switching device, such as a DMOS transistor, permits simplified electronics so that fluid flow in each of the channels can be controlled independently. Preferably, each digital driver is connected to multiple switching devices that each can be used to control the pumping rate of a separate electrode-based pump.

The invention includes employing an electrode-based pump to move reagent selected from the group consisting solutions of amino acids, protected amino acids, nucleotides, protected nucleotides, carbodiimides, reactive derivatives of N-protected amino acids and phosphoamidite derivatives of nucleotides. The carbodiimides are preferably C2 to C12 aryl carbodiimides. The concentration of these reagents is preferably from about 0.01 M to about 0.2 M.

The invention further provides a method of pumping comprising employing an electrode-based pump to move a reagent selected from the group consisting of organic amines, such as C1 to C10 hydrocarbons substituted with an amino group and carboxylic acids, such as C1 to C10 hydrocarbons substituted with a carboxylic acid group. Preferably, the reagent is dissolved in a solvent. In another preferred embodiment, the solvent, in the absence of the reagent, does not pump using a d.c. powered electrode-based pump at a voltage of 2,000 V/mm, more preferably it does not pump using a d.c. powered electrode-based pump at a voltage of 4,000 V/mm..

Features of other distribution systems described in this application can be applied to this embodiment, irrespective of under which subheading they are described.

B. Hydrologic Liquid Distribution System

One structure in which the invention is usefully employed is a hydrologic liquid distribution system made up of a number of reservoirs and a large number of reaction cells, wherein liquid from any given reservoir can be systematically directed to all or a substantial subset of the reactor cells.

Figure 5:
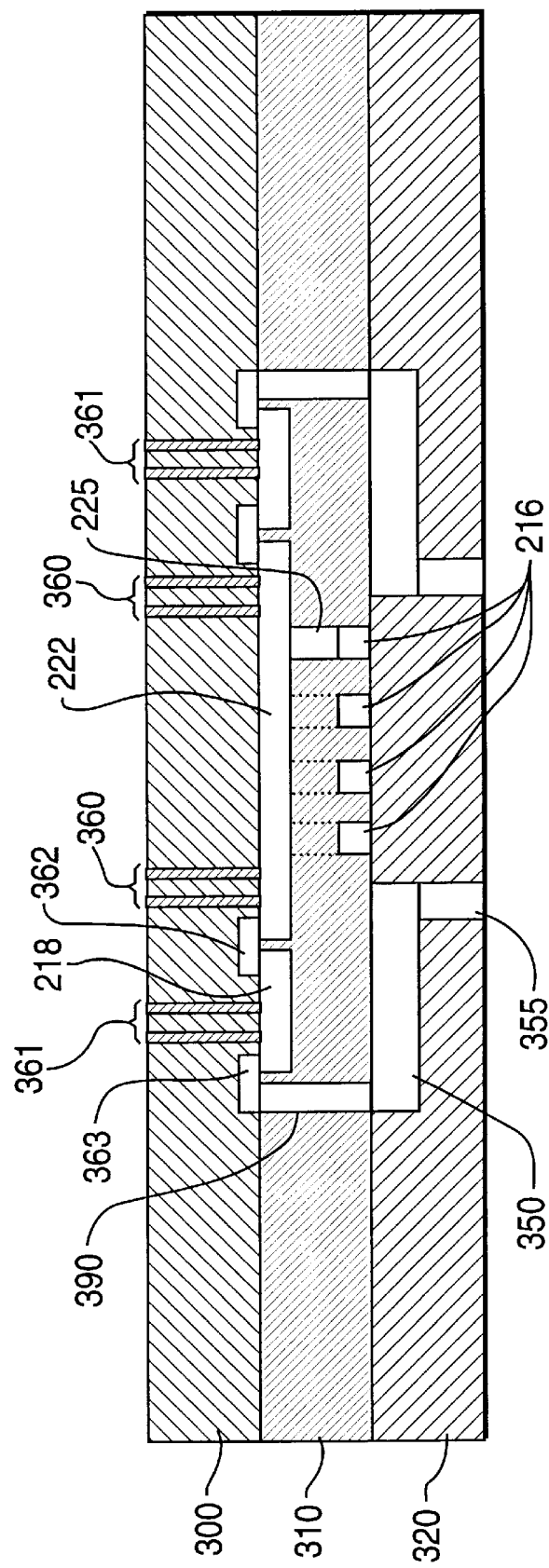
FIG. 5 displays a cut-away view of a liquid distribution system.

Such a liquid distribution system 100 is illustrated in FIGS. 5–10. The distribution system is formed of at least three plates, a feedthrough plate 300, a distribution plate 310 and a reaction cell plate 320 (FIG. 5). The feedthrough plate 300 is bonded to the distribution plate 310. Most importantly, the feedthrough plate 300 has multiple first electrodes 360 and second electrodes 361 that can be manufactured according to the invention. The reaction cell plate 320 is typically removably fitted to the underside of the distribution plate 310, or the underside of intermediate plate 330 interposed between the distribution plate 310 and the reaction cell plate 320.

Figure 6:
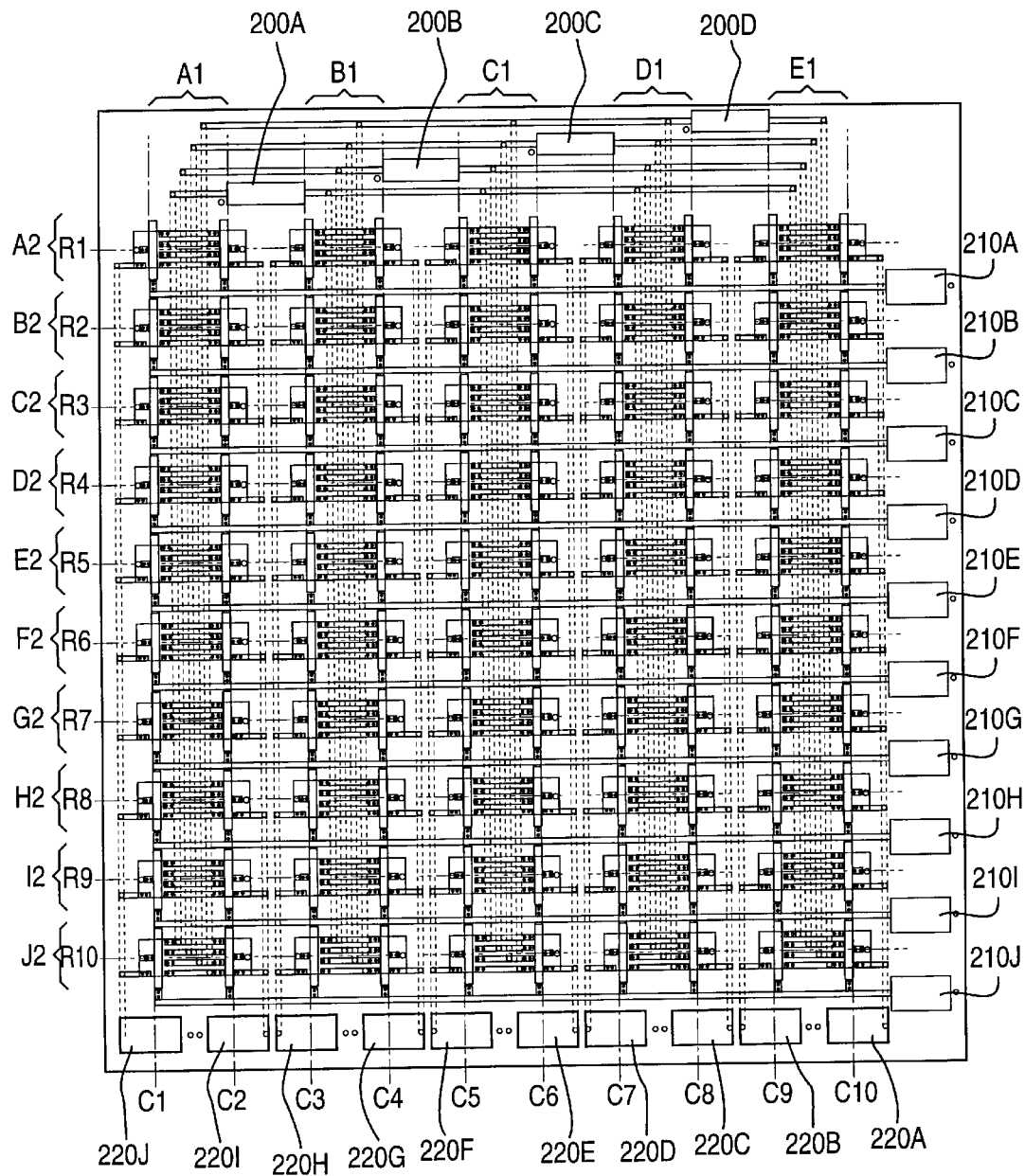
FIG. 6 displays a distribution plate of the liquid distribution system of FIG. 5.
Figure 7:
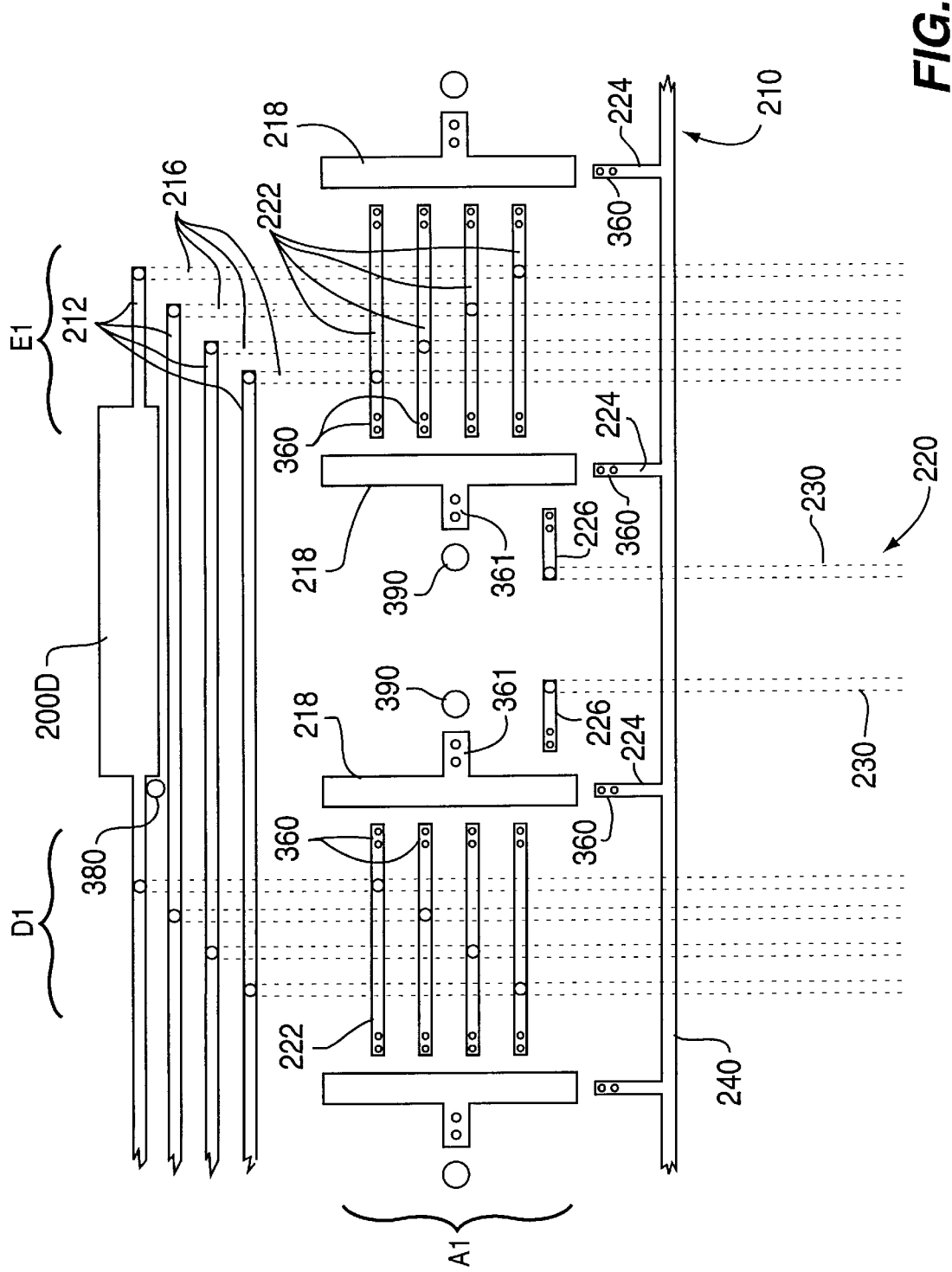
FIG. 7 displays an expanded view of a portion of the distribution plate of FIG. 6.

FIG. 6 shows the layout of a distribution plate 310. FIG. 7 shows an expanded view of a portion of a distribution plate 310 that better illustrates some of the features obscured by the scale of FIG. 6. Typically, the structures indicated in solid lines will be formed in the top layer of the distribution plate 310, while the structures indicated with dotted lines will be formed in the bottom layer of the distribution plate 310, except that in FIG. 6 the reaction cells 350 are indicated by boxes in solid lines even thought these structures are located in a lower plane. Where appropriate, vertical channels connect the structures in the top of the distribution plate 310 with those in the bottom. For convenience, the axis from the top of the illustration to the bottom is designated the NS axis, while the axis from right to left is the EW axis.

At the top of FIG. 6 are four first fluid reservoirs 200A, 200B, 200C and 200D, each having a defined fill level. Each of these first fluid reservoirs 200A, 200B, 200C and 200D has two first reservoir extensions 212 extending along substantially all of an EW axis of the distribution plate 310. The ceilings of the first reservoir extensions 212 preferably are at substantially the same elevation as the first fill level. At five staggered locations, A1, B1, C1, D1 and E1, along the EW axis of the first reservoir extensions 212 there are four first vertical channels 214 (not shown) that connect the first reservoir extensions 212 with four first horizontal feeder channel segments 216 that are formed in the bottom layer of the distribution plate 310. At each staggered location A1, B1, C1, D1 or E1, four adjacent first horizontal feeder channel segments 216, which are connected to separate first reservoir extensions 212, extend along an NS axis to ten positions, A2, B2, C2, D2, E2, F2, G2, H2, I2 and J2. Each position A2, B2, C2, D2, E2, F2, G2, I2 or J2 along the course of each such set of four adjacent horizontal feeder channel segments 216 is adjacent to a pair of reaction cells 350 (not shown). At these positions A2, B2, C2, D2, E2, F2, G2, H2, I2, or J2, the four adjacent first horizontal feeder channel segments 216 are separately connected, via separate second vertical channels 225 (see FIG. 8), to each of four perpendicular first distribution channels 222 formed in the top layer of the distribution plate 310. The ceilings of the first distribution channels 222 define a second fill level that is typically substantially the elevation of the first fill level. The fill level of a distribution channel (e.g., the second fill level) is "substantially" the fill level of the connected reservoir (e.g., the first fill level) if they are offset vertically by no more than about 10% of the depth of the channel; even if the fill levels are further offset vertically they are still substantially the same if filling the reservoir to its fill level results in filling the connected distribution channel and the retention of fluid in the connected distribution channel (for instance, retention due to the capillary barriers described further below with reference to FIG. 8). The combination of a first vertical channel 214, connected to a horizontal feeder channel segment 216, in turn connected to a second vertical channel 225 makes up a first feeder channel 217 (not identified in the Figures).

If liquids are maintained at a defined first level in a first fluid reservoir 200, then substantially the same level will be maintained in the first distribution channels 222 connected to that first fluid reservoir 200 via first feeder channels 217. This equalization occurs due to the principle that two connected bodies of liquid will tend to seek the same level and, where the size of the channels allows, due to capillary flow. Liquids are maintained at a defined level in the first fluid reservoirs. In the illustrated embodiment, liquid is fed into the fluid reservoir 200 through channels in the feedthrough plate 300 and such liquid that is not needed to fill the fluid reservoirs to the defined level is drained through drains 380. First openings 381 (not shown) are formed in the bottom layer of the feedthrough plate 300 to create a liquid connection or sluice between the first fluid reservoirs 200 and the drains 380. Liquids are constantly feed into the first fluid reservoirs 200 (as well as the second fluid reservoirs 210 and third fluid reservoirs 220) typically by the use of an external pump 15 (not shown), such as the model number 205U multichannel cassette pump available from Watson-Marlow, Inc. Alternatively, a defined level can be maintained by monitoring the level of liquid in the first fluid reservoirs 200 (or second fluid reservoirs 210 or third fluid reservoirs 220) and only activating the pumps feeding liquid to a given fluid reservoir when needed to maintain the defined level.

Each set of four adjacent first distribution channels 222 are adjacent to two buffer channels 218, located to each side of the first distribution channels 222 along the EW axis. Liquid can be pumped from any first distribution channel 222 into the adjacent buffer channel 218 by activating the first pump 360 (indicated in FIG. 7 by two filled dots representing the electrodes of one type of pump) of the first distribution channel 222. This pumping creates additional pressure that moves the liquid over capillary barrier 370 (see FIG. 8) separating the first distribution channel 222 and the buffer channel 218. Between each first distribution channel 222, second distribution channel 224 or third distribution channel 226 and the adjacent buffer channel 218 and between each buffer channel 218 and its adjacent third vertical channel 390 (described below) there is such a capillary barrier 370 that inhibits liquid flow when the pumps are not activated. Second openings 362 (see FIG. 8) are formed in the bottom layer of the feedthrough plate 300 to create a liquid connection or sluice between the first distribution channels 222 and the buffer channels 218. From a buffer channel 218, liquid can be pumped using a second pump 361 (indicated in FIG. 8 by two filled dots representing the electrodes of one type of pump) to a third vertical channel 390 that connects with a reaction cell in the reaction cell plate 320. Third openings 363 (see FIG. 8) in the bottom layer of the feedthrough plate 300 or the distribution plate 310 serve to create a liquid connection or sluice between the buffer channels 218 and third vertical channels 390.

Figure 8:
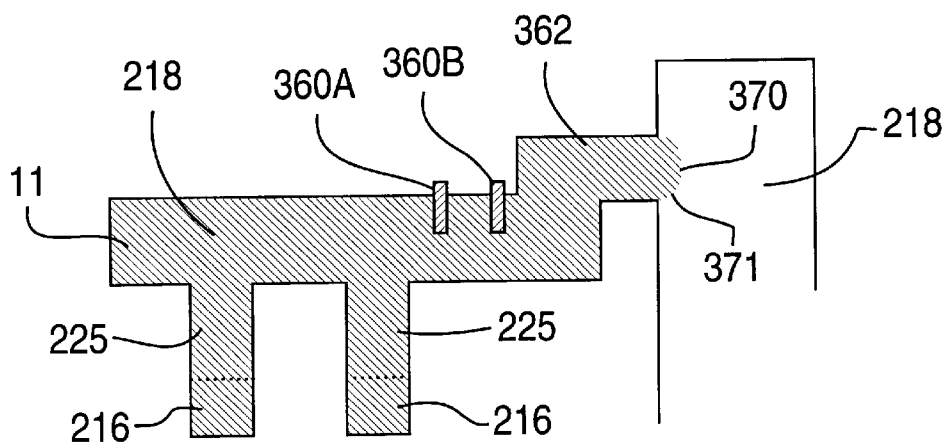
FIG. 8 shows a capillary barrier between a first distribution channel and a buffer channel.
Figure 10:
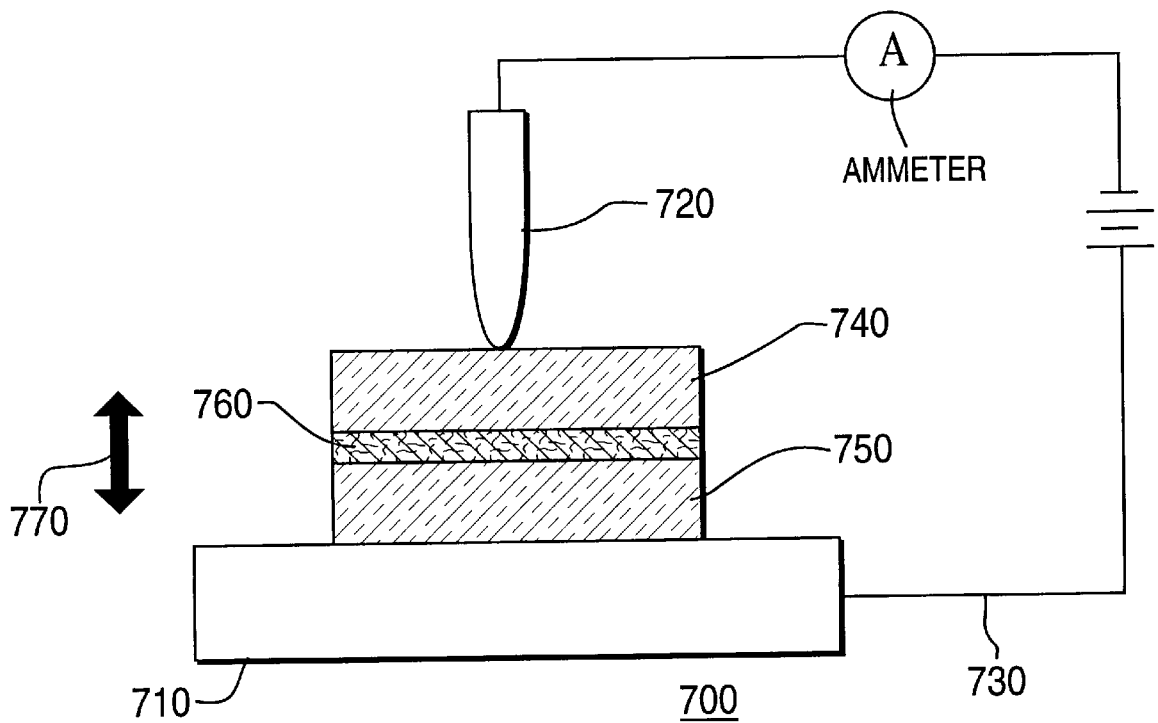
FIG. 10 shows a device for conducting field assisted bonding of plates.

FIG. 8 illustrates a capillary barrier 370, at which a meniscus 371 forms, at the junction between a first distribution channel 222 containing liquid 11 and either a buffer channel 218 or a third vertical channel 390. The meniscus 371 formed at the outlet of first distribution channel 222 into buffer channel 218 will tend to inhibit seepage from the first distribution channel 222, such as the seepage that can result from capillary forces. In some embodiments there are vents (not illustrated) that extend through the feedthrough plate 300 at the tops of buffer channel 218 or third vertical channel 390.

Note that only a small cut-away of NS oriented horizontal feeder channel segments 216 are shown in FIG. 8. Typically, these channels extend inwardly and outwardly from the illustrated cut-away and connect with additional first distribution channels 222 situated to distribute liquid to other reaction cells 350.

Along the right side of the distribution plate 310 are ten second fluid reservoirs 210, each having a second reservoir extension 240 extending along an EW axis. Second distribution channels 224 form "L"-extensions off of second reservoir extensions 240 and are each positioned adjacent to a separate buffer channel 218, such that there are ten second distribution channels 224 extending off of each second reservoir extension 240. Each second distribution channel 224 has a pump 360 that can move liquid from a second distribution channel 224 to the adjacent buffer channel 218. Second openings 362 (not shown) in the bottom of feedthrough plate 300 serve to provide a sluice or route of liquid connection between the second distribution channels 224 and the buffer channels 218. Liquid moves from the buffer channels 218 to the reaction cells as described above. Located adjacent to each second reservoir 210 is a drain 380 (not shown) that operates to maintain a defined third fill level as described above.

As will be described further below in Section D in reference to FIGS. 9A–9D, the capillary barriers 370 and sluices created by the second openings 362 or third openings 363 act as a combined valve and pump. The capillary barriers 370 prevent flow to the reaction cell, which flow would be favored by capillary forces, until the first pumps 360 or second pumps 361 provide the extra pressure needed to overcome the capillary barriers 370. Narrowing the sluices can increase the capillary forces favoring flow, thereby reducing the amount of added pressure needed to overcome the capillary barriers 370. The use of the capillary barriers 370 allows flow control to be governed by the first pumps 360 or second pumps 361, which are typically controlled by controller 10.

Located along the bottom edge of the distribution plate illustrated in FIG. 6 are ten third liquid fluid reservoirs 220. Horizontal feeder channel segments 230 are connected to the third fluid reservoirs 220 and to third distribution channels 226 via fourth vertical channels 227. The third distribution channels 226 have first pumps 360 which can move liquid into adjacent buffer channels 218 via openings 362 (not shown) in the feedthrough plate 300. Located adjacent to each third fluid reservoir 220 is a drain 380 (not shown) that operates to maintain a defined fourth fill level as described above. Third fluid reservoirs 220 and connected third distribution channels 226 operate in just the same way as first fluid reservoirs 200 and first distribution channels 222. Those of ordinary skill in the art will readily envision alternative geometries wherein a number of separate third fluid reservoirs 220 can interact with a given buffer channel 218 via a number of third distribution channels 226 positioned adjacent to the buffer channel 218. Located adjacent to each third reservoir 220 is a drain 380 (not shown) that operates to maintain a defined third fill level as described above.

The above discussion describes the distribution system as being formed with a feedthrough plate 300, distribution plate 310 and reaction cell plate 320. However, it will be clear that additional plates can conveniently be incorporated into the distribution system. For instance, a intermediate plate 330 is, in a preferred embodiment, permanently bonded underneath the distribution plate 310 and interposed between the distribution plate 310 and the reaction cell plate 320. The use of the intermediate plate 330 allows for much greater flexibility in the design of the channels the form the distribution system.

C. Controller

The controller 10 will typically be an electronic processor. However, it can also be a simpler device comprised of timers, switches, solenoids and the like. The important feature of controller 10 is that it directs the activity of the first pumps 360 and second pumps 361 and, optionally, the activity of external pumps 171. A circuit of thin film transistors (not shown) can be formed on the liquid distribution system to provide power to the wells via leads and electrodes, and to connect them with the driving means such as the controller 10, so as to move liquids through the array. Pins can also be formed substrate which are addressable by logic circuits that are connected to the controller 10 for example.

D. Capillary barriers

Capillary barriers have been described above with reference to FIG. 8. However, more complex design considerations than were discussed above can, in some cases, affect the design of the capillary barrier. In some cases it is desirable to narrow the sluice formed by second opening 362 or third opening 363 to increase the impedance to flow (i.e., the frictional resistance to flow) as appropriate to arrive at an appropriate flow rate when the associated first pump 360 or second pump 361 is activated. Such a narrowing is illustrated by comparing the sluice of FIG. 9A with the narrowed sluice of FIG. 9D. The problem that this design alteration can create is that narrower channels can increase capillary forces, thereby limiting the effectiveness of channel breaks.

Thus, in one preferred embodiment, a channel break further includes one or more upwardly oriented sharp edges 369, as illustrated in FIGS. 9B and 9C. More preferably, a channel break includes two or more upwardly oriented sharp edges 369. In FIG. 9B, portion 362A of opening 362 is cut more deeply into first plate 300 to create an open space useful for the operation of upwardly oriented sharp edges 369.

E. Fabrication of Plates, Channels, Reservoirs and Reaction Cells

The liquid distribution systems of the invention can be constructed a support material that is, or can be made, resistant to the chemicals sought to be used in the chemical processes to be conducted in the device. For all of the above-described embodiments, the preferred support material will be one that has shown itself susceptible to microfabrication methods that can form channels having cross-sectional dimensions between about 50 microns and about 250 microns, such as glass, fused silica, quartz, silicon wafer or suitable plastics. Glass, quartz, silicon and plastic support materials are preferably surface treated with a suitable treatment reagent such as chloromethylsilane or dichlorodimethylsilane, which minimize the reactive sites on the material, including reactive sites that bind to biological molecules such as proteins or nucleic acids. As discussed earlier, the expansion valve liquid distribution system is preferably constructed of a plastic. In embodiments that require relatively densely packed electrical devices, a non-conducting support material, such as a suitable glass, is preferred. Corning 211 borosilicate glass, Corning 7740 borosilicate glass, available from Corning Glass Co., Corning, N.Y., are among the preferred glasses.

The liquid distribution system of the invention is preferably constructed from separate plates of materials on which channels, reservoirs and reaction cells are formed, and these plates are later joined to form the liquid distribution system. This aspect of the invention is described in some detail with respect to the hydrologic liquid distribution system. Preferably, the reaction cell plate, e.g. reaction cell plate 320, is the bottom plate and is reversibly joined to the next plate in the stack. The other plates forming the distribution system, which preferably comprise two to three plates are preferably permanently joined. This joinder can be done, for instance, using adhesives, such as glass-glass thermal bonding.

One preferred method of permanently joining the plates is to first coat the plate with a layer of glass glaze generally having a thickness between about 50 microns and about 500 microns, more preferably between about 75 microns and about 125 microns. The above thicknesses contemplate that substantial amounts of channel structure will be formed in the glaze layer. Otherwise, the glaze generally has a thickness between about 1 microns and about 100 microns, more preferably between about 10 microns and about 25 microns. These methods are preferably applied to join glass plates. Suitable glazes are available from Ferro Corp., Cincinati, Ohio. The glazed plate is treated to create channels, reservoirs, or reaction cells as described below. The glazed plate is positioned against another plate, which preferably is not glazed, and the two plates are heated to a temperature of about the softening temperature of the glaze or higher, but less than the softening temperature for the non-glaze portion of the plates.

Another preferred method of permanently joining glass plates uses a field assisted thermal bonding process. It has now been discovered that glass-glass sealing using field assist thermal bonding is possible despite the low conductivity of glass if a field assist bonding material is interposed between the plates to be bonded.

To the top or bottom surface of one glass plate a layer of a field assist bonding material is applied. Preferably, the field assist bonding material layer has a thickness between about 50 nm and about 1,000 nm, more preferably, between about 150 nm and about 500 nm. The field assist bonding material can be a material capable of bonding glass plates pursuant to the method described herein. Preferably, the field assist bonding material is silicon or silica. More preferably, the field assist bonding material is silicon.

The field assist bonding material can be applied to a plate, for instance, by chemical vapor deposition or by a sputtering process where surface molecules are emitted from a cathode when the cathode is bombarded with positive ions from a rare gas discharge and the surface molecules collide with and bond to a nearby substrate. Pursuant to the present invention, silicon layers of between about 150 nm and about 500 nm thickness have been bonded to glass plates under conditions that can be expected to generate an outer surface layer of silicon dioxide, such as an about 20 Å layer, although the sealing process is believed to be effective in the absence of this layer. The coated plate is treated, as needed, to create channels, reservoirs, or reaction cells using the method described below. Alternatively, the plate was so treated prior to coating with the field-assist bonding material. The coated plate is then positioned against another plate, which preferably is not coated, and placed in a field assisted bonding device 700 such as that illustrated in FIG. 9. The field assisted bonding device 700 has a heating device 710, such as a heating plate. The field assisted bonding device 700 further has an electrode 720 and a ground 730 that allows a voltage to be applied across the first plate 740 and the second plate 750, to which has been applied a layer of silicon 760. Generally, the field assisted bonding is conducted under a normal atmosphere.

The plates are brought to a temperature effective when an appropriate electric field is applied across the plates effective to accelerate the bonding process. While not wishing to be bound by theory, it is believed that the combination of a cathode applied to the first glass plate 740 and the greater exchange-site mobility of ions (such as sodium ions) caused by the elevated temperature causes an ion depletion on the face of the first glass plate 740 opposite that to which the cathode is applied. The ion depletion, it is believed, causes a surface charge at the bottom surface of first glass substrate 740, which correlates with the creation of a strong localized electrostatic attraction for the second substrate 750. It is clear that this process creates strong bonding between the substrates and, it is believed that this is due to the formation of chemical bonds between the silica of the first glass substrate 740 and the silicon coated onto the second glass substrate 750. Preferably, the temperature is brought to from about 200° C. to about 600° C., more preferably from about 300° C. to about 450° C. During the process an voltage typically from about 200 V to about 2,500 V, preferably from about 500 V to about 1500 V, is applied across the first glass plate 740 and second glass plate 750. The voltage most suitably applied varies with the thickness of the glass plates. The voltage pulls the first glass plate 740 and second glass plate 750, including the silicon layer 760 applied to one of the plates, into intimate contact. Typically, hermetic sealing is achieved within minutes to about an hour, depending on the planar dimensions of the glass plates. The time required to achieve adequate sealing varies with, among other things, the smoothness of the plates, the electrical field strength, the temperature, and the dimensions of the plates. Bonding between the plates is typically apparent visually, since it is accompanied by the disappearance of the interface between the plates and the formation of gray color at the bonded regions that can be seen when an observer looks through the thinner dimensions of the two plates.

The method described above can be used to bond a glass substrate to another glass substrate and to a third glass substrate simultaneously.

Those of ordinary skill will recognize that while a hot plate is illustrated as providing the heating for the thermal assisted bonding, other heating devices, including ovens, may be used. It will also be realized that it is desirable to match, when possible, the coefficients of thermal expansion of the substrates to be bonded.

The reservoirs, reaction cells, horizontal channels and other structures of the fluid distribution system can be made by the following procedure. A plate, that will for instance make up one of feedthrough plate 300, distribution plate 310, reaction cell plate 320 or intermediate plate 330, is coated sequentially on both sides with, first, a thin chromium layer of about 500 angstroms thickness and, second, a gold film about 2000 angstroms thick in known manner, as by evaporation or chemical vapor deposition (CVD), to protect the plate from subsequent etchants. A two micron layer of a photoresist, such as Dynakem EPA of Hoechst-Celanese Corp., Bridgewater, N.J., is spun on and the photoresist is exposed, either using a mask or using square or rectangular images, suitably using the MRS 4500 panel stepper available from MRS Technology, Inc., Acton, Mass. After development to form openings in the resist layer, and baking the resist to remove the solvent, the gold layer in the openings is etched away using a standard etch of 4 grams of potassium iodide and 1 gram of iodine ($I_2$) in 25 ml of water. The underlying chromium layer is then separately etched using an acid chromium etch, such as KTI Chrome Etch of KTI Chemicals, Inc., Sunnyvale, Calif. The plate is then etched in an ultrasonic bath of $HF-HNO_3-H_2O$ in a ratio by volume of 14:20:66. The use of this etchant in an ultrasonic bath produces vertical sidewalls for the various structures. Etching is continued until the desired etch depth is obtained. Vertical channels are typically formed by laser ablation.

The various horizontal channels of the distribution system embodiments typically have depths of about 50 microns to about 250 microns, preferably from about 50 microns to about 100 microns, more preferably from about 50 microns to about 80 microns. In an alternative embodiment, the preferred depths are from about 150 microns to about 400 microns. The widths of the horizontal channels and the diameters of the vertical channels are typically from about 50 microns to about 200 microns, preferably from about 100 microns to about 200 microns, more preferably from about 120 microns to about 150 microns.

F. Fabrication of Electrode-Based Pumps

In many embodiments, the liquid distribution systems of the invention require the formation of numerous electrodes for pumping fluids through the liquid distribution system. These electrodes are generally fabricated in the top glass plate of the liquid distribution system. Typically each pair of electrodes is closely spaced (e.g. 50 to 250 microns separation). The electrodes are fabricated with diameters of preferably about 25 microns to about 150 microns, more preferably about 50 microns to about 75 microns. In preferred embodiments, the liquid distribution system has 10,000 reaction cell 350 with each reaction cell 350 having 6–10 associated electrode-based pumps. Thus, a liquid distribution system can require about 200,000 to about 300,000 electrodes. To produce such structures using mass production techniques requires forming the electrodes in a parallel, rather than sequential fashion. A preferred method of forming the electrodes involves forming the holes in the plate (e.g., feedthrough plate 300) through which the electrodes will protrude, filling the holes with a metallic thick film ink (i.e., a so-called "via ink", which is a fluid material that scinters at a given temperature to form a mass that, upon cooling below the scintering temperature, is an electrically conductive solid) and then firing the plate and ink fill to convert the ink into a good conductor that also seals the holes against fluid leakage. The method also creates portions of the electrodes that protrude through the plate to, on one side, provide the electrodes that will protrude into the liquids in fluid channels and, on the other side, provide contact points for attaching electrical controls.

For example, holes are drilled in 500 micron thick plates of borosilicate glass using an excimer laser. Holes having diameters between 50 and 150 microns are then filled with thick film inks, using an commercial Injection Via-fill Machine (Pacific Trinetics Model #VF-1000, San Marcos, Calif.). It has been unexpectedly discovered that only select formulations of via inks sufficiently function to fill such high aspect ratio holes such that the fired ink adheres to the sides of the holes, does not crack during the firing process, and seals the holes against fluid flow. One parameter that is important to so forming sealed, conductive conduits through high aspect holes is selecting metal powder and glass powder components for the via ink that have sufficiently fine dimensions. One parameter that is important to so forming sealed, conductive conduits through high aspect holes is selecting metal powder and glass powder components for the via ink that have sufficiently fine dimensions. One suitable formulation uses: 12-507 Au powder (Technic Inc., Woonsocket, R.I.), 89.3% w/w; F-92 glass (0. Hommel Co., Carnegie, Pa.), 5.7% w/w; 15% w/v ethyl cellulose N-300 (N-300, Aqualon, Wilmington, Del.) in Texanol™ (monoisobutarate ester of 2,2,4-trimethyl-1,3-pentandiol, Eastman Chemical Products, Kingsport, Tenn.), 2.4% w/w; 15% w/v Elvacite $_{2045}$™ (polyisobutyl methacrylate) in Terpineol T-318 (mixed tertiary terpene alcohols, Hercules Inc., Wilmington, Del.), 2.1% w/w; and Duomeen TDO™ (N-tallow alkyl trimethylenediamine oleates, Akzo Chemicals, Chicago, Ill.), 0.5% w/w. The gold powder from Technic, Inc. has an average particle diameter of 0.9 microns. Another suitable formulation uses: Ag Powder Q powder (Metz, South Plainfield, N.J.), 80.8% w/w; F-92 glass (O. Hommel Co. Carnegie, Pa.), 5.2% w/w; VC-1 resin (37% w/w Terpineol T-318, 55.5% w/w butyl carbitol, 7.5% w/w ethylcellulose N-300, Aqualon, Wilmington, Del.), 3.7% w/w; 15% w/v ethyl cellulose N-300 in Texanol™, 4.0% w/w; 15 % w/v Elvacite $_{2045}$™ (polyisobutyl methacrylate) in Terpineol T-318, 4.1 % w/w; Duomeen TDO™, 0.6% w/w; and Terpineol, 1.6% w/w. These formulations were fired at 550° C. to form high aspect ratio conductive conduits.

When the size of the glass or metal powders increases, good filling properties (lack of cracking, good sealing against liquids, good adherence to sides of hole) can often still be obtained by decreasing the amount of organic in the via ink.

The devices used to insert via inks into holes in a plate typically include a metal stencil with openings corresponding to the openings in the plate. Via ink is applied above the stencil, which rests on the plate, and a bladder device is used to pressurize the ink to force it to fill the holes. After filling, the plate with its via ink-filled holes is removed for further processing, as described below.

Prior to firing, much of the organic component is evaporated away by, for example, placing the ink-filled plate in a oven (e.g. at 100° C.) for one to five minutes. Preferably, the firing is conducted at a temperature from about 450° C. to about 700° C., more preferably from about 500° C. to about 550° C. However, the upper end of the appropriate firing temperature range is primarily dictated by the temperature at which the plate being treated would begin to warp. Accordingly, with some types of plates much higher temperatures could be contemplated.

To assure that there is conductive material that protrudes above and below the glass plate after firing, the top and bottom surface of the plate can be coated with a sacrificial layer of thicknesses equaling the length of the desired protrusions. The sacrificial layers can be applied before or after the holes are formed in the plate. If before, then the holes are formed through both the glass plate and the sacrificial layers. If after, then (a) corresponding openings through the sacrificial layers can be created by creating a gas pressure difference from one side of the plate to the other, which pressure difference blows clear the sacrificial material covering the holes or (b) such openings through at least the top sacrificial layer are created when the pressure of the ink pushes through the sacrificial layer and into the holes (leaving an innocuous amount of sacrificial layer material in the holes). An appropriate sacrificial layer burns away during the firing process. Sacrificial layers can be made coating a plate with, for instance, 5–25 w/w % mixtures of ethyl cellulose resin (e.g., Ethyl Cellulose N-300, Aqualon, Wilmington, Del.) dissolved in Terpineol T-318™ or Texanol™, or 5–50% w/w mixtures of Elvacite $_{2045}$™ in Terpineol T-318™. After firing, the surfaces of the electrode can be enhanced plating metals, such as nickel, silver, gold, platinum, rhodium, etc. The depositions can be performed using standard electrolytic and/or electroless plating baths and techniques.

Preferably, where a plate that is to contain etched holes will be processed to include electrodes, the etching occurs first, followed by coating with the sacrificial layer and forming the holes.

In an alternate method of manufacture, for each pump, two or more metal wires, for example gold or platinum wires about 1–10 mils in diameter, are inserted into the openings in the channel walls about, e.g., 150 microns apart. The wires were sealed into the channels by means of a conventional gold or platinum via fill ink made of finely divided metal particles in a glass matrix. After applying the via fill ink about the base of the wire on the outside of the opening, the channel is heated to a temperature above the flow temperature of the via fill ink glass, providing an excellent seal between the wires and the channel. The via ink, which is used to seal the holes, can be substituted with, for instance, solder or an adhesive.

In an alternate method of manufacture, for each pump, two or more metal wires, for example gold or platinum wires about 1–10 mils in diameter, are inserted into the openings in the channel walls about, e.g., 150 microns apart. The wires were sealed into the channels by means of a conventional gold or platinum via fill ink made of finely divided metal particles in a glass matrix. After applying the via fill ink about the base of the wire on the outside of the opening, the channel is heated to a temperature above the flow temperature of the via fill ink glass, providing an excellent seal between the wires and the channel.

G. Drivers

An analog driver is can be used to vary the voltage applied to the electrode-based pump from a DC power source. A transfer function for each fluid is determined experimentally as that applied voltage that produces the desired flow or fluid pressure to the fluid being moved in the channel. However, an analog driver is required for each pump along the channel and is suitably an operational amplifier. Typically, however, a separate analog driver is required for each electrode-based pump. This is impractical when a large number of channels are to be controlled.

Thus a digital driver having a pulse of suitable voltage amplitude and that can provide gating control to the electrodes is preferred for use herein. Control of fluid flow is accomplished by applying pulses of different pulse widths and different repetition rates to the electrodes. A typical pulse train is shown in FIG. 1 wherein $t_1$ is the pulse width and $t_2$ is the distance between pulses.

Figure 11:
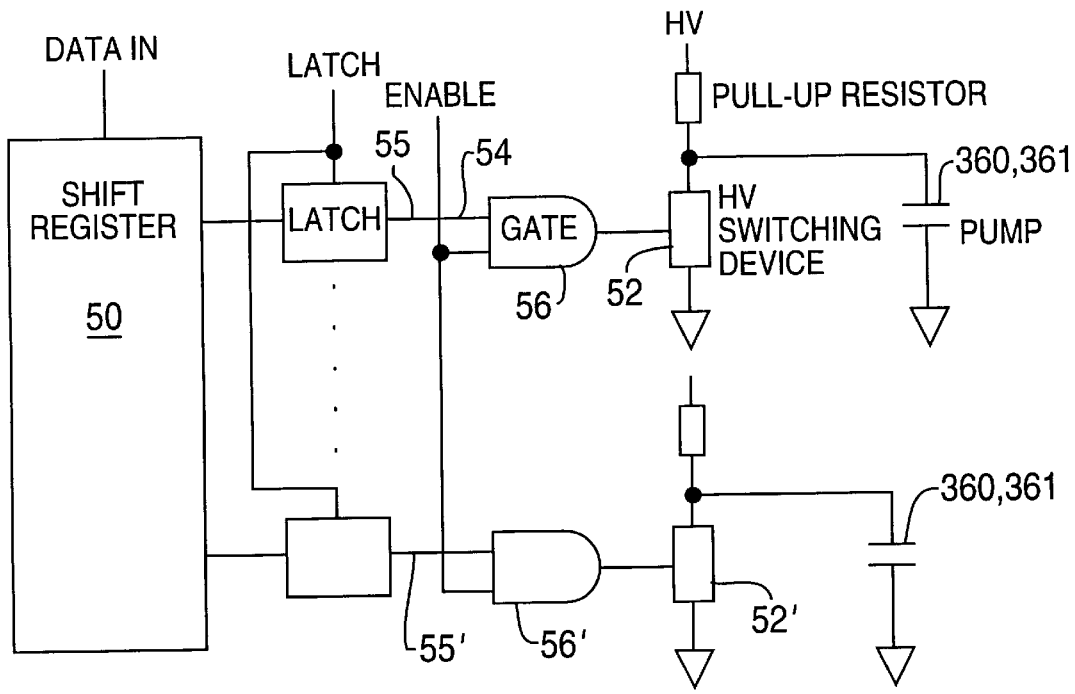
FIG. 11 shows a digital driver for powering the electrode-based pumps.

FIG. 11 illustrates one configuration for providing control of fluid flow of a plurality of channels simultaneously and independently. The data generated for the above variables, as obtained experimentally for various fluids and electrodes, is loaded into a controller 10 (not shown), such as a computer. The controller converts the data to instructions for the digital driver to a first pump 360 or second pump 361. The data is transferred to the digital driver and is stored in the shift register 50. Different switching devices 52 attached to each electrode pair can be selected, independently of each other, depending on the state of the latch output. The switching devices are turned on and off by an enabling signal 54 and a latch output signal 55 applied to an AND gate 56. A pulse of a particular width and repetition rate is applied to the enable signal 54 which determines the length of time the switch is on or off. Thus the fluid flow in the channel can be controlled using a signal having constant amplitude but variable pulse width and repetition rate. By preselecting the pulse repetition rate, a predetermined applied voltage is selected for each first pump 360 or second pump 361 in a channel 10.

An array of the above switching devices 52 can be connected to the shift register 50 for controlling the fluid flow of an array of channels, each switching device controlling the fluid flow in a different channel. A single switching device 52', connected to the shift register 50 through a gate 56', an enable signal 54' and a latch signal 55', is shown for simplicity in FIG. 5, but a plurality of switching devices will be used, one for each pump in the array of channels.

H. Reaction Cells and Reaction Cell Plate

Reaction cells 350 are typically depressions formed in the upper layers of a reaction cell plate 320. The drain 355 to a reaction cell 350 can be open at the bottom of the reaction cell 350, in which case drainage is controlled kinetically and by negative pressure from the connected channels.

Drains are optional, since in some uses the amount of liquid moved into a reaction cell 350 is less than the reaction cell's volume. If drains are absent, however, vents are required. Vents for the reaction cells 350 are appropriate in other contexts.

The reaction cell plate can be reversibly bonded to the next higher plate by, for instance, assuring that the two surfaces are smoothly machined and pressing the two plates together. Or, for example, a deformable gasket, such as a teflon, polyethylene or an elastomoric film (such as a natural rubber, ABS rubber, or polyurethane elastomor film) gasket is interposed between the plates. One way to maintain a force adhering the plates against the gasket is to have a number of vacuum holes cut through the bottom plate and the gasket and applying a vacuum at these locations. Generally, the seal should be sufficient so that the pump used to form the vacuum can be shut down after initially forming the vacuum. The gasket is preferably from about 0.0×5 mils to about 1 mil, more preferably from about 0.1 mils to about 0.3 mils in thickness.

Fluid exiting the bottom of the reaction cell plate 320 can, for instance, simply collect in a catch pan or it can diffuse into a porous substrate such a sintered glass, glass wool, or a fabric material. Alternately, a fifth plate [340] is attached to the underside of the reaction cell and has channels that connect the outlets of the reaction cells 350 to individual collection reservoirs from which fluid can be sampled. For instance, the fifth plate [340] is wider than the reaction cell plate 320 and the collection reservoirs are located at the top surface of the fifth plate 340 in the area not covered by the reaction cell plate 320.

Preferably, synthetic processes conducted in the reaction cells 350 of the liquid distribution system will take place on insoluble supports, typically referred to as "beads", such as the styrene-divinylbenzene copolymerizate used by Merrifield when he introduced solid phase peptide synthetic techniques. Merrifield, *J. Am. Chem. Soc.* 85: 2149,1963. See, also Barany et al., "Recent Advances in Solid-Phase Synthesis," in *Innovation and Perspectives in Solid Phase Synthesis: Peptides, Polypeptides, and Oligonucleotides*, Roger Epton, Ed., collected papers of the 2nd International Symposium, Aug. 27–31, 1991, Canterbury, England, p. 29. These supports are typically derivatized to provide a "handle" to which the first building block of an anticipated product can be reversibly attached. In the peptide synthesis area, suitable supports include a p-alkoyxbenzyl alcohol resin ("Wang" or PAM resin) available from Bachem Bioscience, Inc., King of Prussia, Pa.), substituted 2-chlorotrityl resins available from Advanced Chemtech, Louisville, Ky., and polyethylene glycol grafted poly styrene resins (PEG-PS resins) are available from PerSeptive Biosystems, Framingham, Mass. or under the tradename TentaGel, from Rapp Polymere, Germany. Similar solid phase supports, such as polystyrene beads, are also used in the synthesis of oligonucleotides by the phosphotriester approach (see Dhristodoulou, "Oligonucleotide Synthesis: Phosphotriester Approach," in *Protocols for Oligonucleotide Conjugates*, S. Agrawal, Ed., Humana Press, N.J., 1994), by the phosphoramidite approach (see Beaucage, "Oligodeoxynucleotide Synthesis: Phosphoramidite Approach," in *Protocols for Oligonucleotide Conjugates*, S. Agrawal, Ed., Humana Press, N.J., 1994), by the H-phosponate approach (see Froehler, Oligodeoxynucleotide Synthesis: H-Posponate Approach," in *Protocols for Oligonucleotide Conjugates*, S. Agrawal, Ed., Humana Press, N.J., 1994), or by the silyl-phosphoramidite method (see Damha and Ogilvie, Oligodeoxynucleotide Synthesis: "Silyl-Phosphoramidite Method," in *Protocols for Oligonucleotide Conjugates*, S. Agrawal, Ed., Humana Press, N.J., 1994). Suitable supports for oligonucleotide synthesis include the controlled pore glass (cpg) and polystyrene supports available from Applied Biosystems, Foster City, Calif. Solid supports are also used in other small molecule and polymeric organic syntheses, as illustrated in oligocarbamate synthesis for organic polymeric diversity as described by Gorden et al., *J Medicinal Chem.* 37: 1385–1401, 1994.

Preferably, the reaction cells 350 are rectangular with horizontal dimensions of about 400 microns to about 1200 microns, more preferably about 500 microns to about 1000 microns, yet more preferably about 640 microns, and a depth of about 200 microns to about 400 microns. Where beads will be used in the reaction cells 350, the depth of the reaction cells 350 is preferably at least about 50 microns greater than the swelled diameter of the beads. The support beads typically used as in solid-phase syntheses typically have diameters between about 50 microns and about 250 microns, and reactive site capacities of between about 0.1 mmoles/g and about 1.6 mmoles/g. Typically, between about 1 and about 10 of such beads are loaded into a reaction cell 350 to provide a desired capacity of between about 1 nmole and about 10 nmole per reaction cell 350. Recently, beads have become available that have a diameter that ranges between about 200 microns and about 400 microns, depending on the solvent used to swell the beads and the variation in size between the individual beads, and a reactive site capacity of between about 5 nmole and about 20 nmole per bead have become available. These large beads include the beads sold by Polymer Laboratories, Amhearst, Mass. Desirable reactive site finctionalities include halogen, alcohol, amine and carboxylic acid groups. With these large beads, preferably only one bead is loaded into each reaction cell 350.

Another option for creating a solid support is to directly derivatize the bottom of the reaction cell 350 so that it can be reversibly coupled to the first building block of the compound sought to be synthesized. The chemistry used to do this can be the same or similar to that used to derivatize controlled pore glass (cpg) beads and polymer beads. Typically, the first step in this process is to create hydroxyl groups (if they do not already exist on the support) or amino groups on the support. If hydroxyl groups exist or are created, they are typically converted to amino groups, for instance by reacting them with gamma-aminopropyl triethoxy silane. Flexible tethers can be added to the amino groups with cyclic acid anhydrides, reactions with polymerized alkylene oxides and other methods known to the art. Examples of such methods are described in Fields et al., "Synthetic Peptides: A User's Guide," W. H. Freeman and Co., Salt Lake City, Utah, 1991.

Methods of creating reactive sites include, for the case where the reaction cell plate 320 is made of plastic, exposing the bottom of the reaction cells 350 to a reactive plasma, such as that created by a glow-discharge in the presence of ammonia or water, to create $NH_2$ groups. Such procedures are described in "Modification of Polymers," Carraher and Tsuda, eds., American Chem. Soc., Washington, D.C., 1980. Another method, useful with glass, ceramic or polymeric substrates, is depositing a film of silicon monoxide by vapor deposition at low temperature to create hydroxyl functionalities. Glass surfaces can be treated with alkali, for instance with KOH or NaOH solutions in water or water/alcohol mixtures, to expose hydroxyl functional groups. Non-annealed borosilicate glass surfaces, including coatings of non-annealed borosilicate glass created by chemical vapor deposition, can be etched, for instance with hydrofluoric acid dissolved in water, to dissolve the regions that are rich in boron, which process creates a porous structure with a large surface area. This porous structure can be treated with alkali to expose hydroxyl groups. The degree of reactive site substitution on such surfaces is preferably at least about 83 nmoles per $cm^2$, more preferably at least about 124 nmoles per $cm^2$ (implying a substitution in 500 micron by 500 micron reaction cell 350 of at least about 0.31 nmole), yet more preferably at least about 256 nmoles per $cm^2$.

The above described methods for using the bottom of the reaction cells 350 as a solid support can be supplemented by methods that increase the surface area of the bottom of the reaction cells 350. One method is to create columnar structures of silicon monoxide, for instance by thermal evaporation of $SiO_x$. Another such method is to insert into the reaction cells fabrics, such as non-woven glass or plastic (preferably fiberglass or polypropylene fiber) fabrics and plasma treating the fabric to create reactive sites.

Another method uses spin-on glass, which creates a thin film of nearly stoichiometric $SiO_2$ from a sil-sesquioxane ladder polymer structure by thermal oxidation. Sol-gel processing creates thin films of glass-like composition from organometallic starting materials by first forming a polymeric organometallic structure in mixed alcohol plus water and then careful drying and baking. When the sol-gel system is dried above the critical temperature and pressure of the solution, an aerogel results. Aerogels have chemical compositions that are similar to glasses (e.g. $SiO_2$) but have extremely porous microstructures. Their densities are comparably low, in some cases having only about one to about three percent solid composition, the balance being air.

I. Miscellaneous Features

In the case where the temperature of a particular well is to be monitored or changed, a means of heating or cooling the well is built into the well, as will be further explained below with reference to FIG. 20. The first well 36 in this example has deposited on its bottom surface a thin film 57 of a suitable metal oxide, such as tin oxide or indium tin oxide. The thin film 57 is connected by means of an electrically conductive metal connection 58 to the end or outer edge of the well 36. The tin oxide coating 57 serves as a heater element for the well 36. The sides of the well 36 have a surface bimetal film 59 and leads 60, suitably made of chromel-alumel alloys, forming a thermocouple to measure the temperature in the well when a source of current is applied to the tin oxide coating 57 and to the leads 58. A voltage applied to the well 36 via electrodes 56 deposited on the backside as shown regulates the temperature in the well. The amount of current applied can be regulated by the controller 10 in response to the temperature measured through the leads 60.

In some applications of the liquid distribution system a significant vapor pressure may develop in reaction cell 350, causing a back pressure into the distribution plate 310. Thus preformed valves 70 (see FIG. 21A) formed of bimetallic materials as described by Jerman et al, "Understanding Microvalve Technology", Sensors, September 1994 pp 26–36 can be situated in third vertical channel 390. These materials have a thermal expansion mismatch. When the temperature in the reaction cell 350 is low, the ball valve 62 is in its normal position permitting free flow of fluids into the well 36 (see FIG. 21A). As the temperature in the well 36 increases, the ball valve 62 moves to a cooler position (FIG. 21B) blocking the third vertical channel 390 to isolate the reaction cell 350, thereby preventing fluids from passing into and out of the first well 36. Alternatively, a conventional check valve having a bearing, such as a bearing made of quartz or polytetrafluoroethylene polymer can be used to isolate the reaction cell 350. Where it is important to have the capability to have fluid flow counter to the direction established by the check valve, the check valve can have an insulating or magnetic bearing, which can be moved to allow such counter-flow with externally applied electrostatic-or magnetic fields.

Other features of liquid distribution systems are described in an application filed Nov. 9, 1995 entitled, "Liquid Distribution System," U.S. application Ser. No. 08/556,036, which application is a continuation-in-part of U.S. application Ser. No. 08/338,703, titled "A Partitioned Microelectronic and Fluidic Device Array for Clinical Diagnostics and Chemical Synthesis," filed Nov. 10, 1994, a continuation-in-part of U.S. application Ser. No. 08/469,238, titled "Apparatus and Methods for Controlling Fluid Flow in Microchannels," filed Jun. 6, 1995 and a continuation-in-part of U.S. application Ser. No. 08/483,331, titled "Method and System for Inhibiting Cross-Contamination in Fluids of Combinatorial Chemistry Device," filed Jun. 7, 1995. The disclosure of this Nov. 9, 1995 application entitled "Liquid Distribution System" and of all the above-recited priority filings named in the Nov. 9, 1995 application are incorporated herein by reference in its entirety.

EXAMPLES

Example 1

Liquids Pumped with a Simple Electrode-based Pump

Using the 1 mm capillary with a two electrode-pump described above in Section B.ii., a number liquids have been tested, including the following solvents:

| Solvent | Flow direction | voltage applied |
|---|---|---|
| N-methyl-pyrrolidinone (NMP) | + | 1470 |
| Dimethyl formamide (DMF) | + | 390 |
| Dichloromethane (DCM) | − | 686 |
| Methanol (MeOH) | − | 489 |
| Isopropanol (IPA) | + | |
| Acetone | + | |
| Acetonitrile | + | |

The following solutions in NMP, at 0.1M unless otherwise indicated, have been tested:

| Reagent | Flow direction |
|---|---|
| trans-4-(trifluoromethyl)-cinnamic acid | − |
| 5-benzimidazolecarboxylic acid | − |
| N,N-dicyclohexylcarbodiimide | + |
| isobutylamine | + |
| 2-(1H-benzotriazole-1-yl)-1,1,3,3-tetramethyluronium hexafluorophosphate (HBTU) | No flow at 0.1M, flow occurs lower concentrations (0.01–0.1 M) |

The following solutions in DMF, all at 0.1M excepting piperidine, which was 20% v/v, have been tested:

| Reagent | Flow direction* |
|---|---|
| p-carboxybenzenesulfonamide | −P |
| 4-fluorophenylacetic acid | −P |
| 4-methoxyphenylacetic acid | −P |
| m-trifluoromethylbenzoic acid | −P |
| 3-(4-methoxyphenyl)propionic acid | − |
| 4-bromocinnamic acid | −P |
| terephthalic acid | −P |
| isophthalic acid | −P |
| 1,3-phenylenediacetic acid | −P |
| 1,4-phenylenediacetic acid | −P |
| 3-(4-carboxyphenyl)propionic acid | −P |
| 1,4-phenylenedipropionic acid | −P |
| 4,4'-oxybis (benzoic acid) | −P |
| 4,4'-dicarboxybenzophenone | −P |
| piperidine | + |
| 1,3-diisopropylcarbodiimide | + |
| allylamine | + |
| butylamine | + |
| isoamylamine | + |
| propylamine | + |
| isobutylamine | + |
| cyclohexylamine | + |
| heptylamine | + |
| benzylamine | + |
| phenylamine | +P |
| 3-amino-1-propanol | +P |
| 2-aminoethanol | + |
| 4-(aminomethyl) pyridine | +P |
| 4-(2-aminoethyl) morpholine | +P |
| 1-(3-aminopropyl) imidazole | + |
| triphenylphosphine | + |
| 4-(aminopropyl) morpholine | + |
| 9-fluorenemethanol | + |
| p-nitrobenzyl alcohol | + |
| p-(methylthio) benzyl alcohol | + |
| o-aminobenzyl alcohol | + |
| 2-methoxybenzyl alcohol | + |
| 2-(triflouromethyl) benzyl alcohol | + |
| 2-amino-3-phenyl-1-propanol | +P |
| diethyiazodicarboxylate | −P |
| 4-dimethylaminopyridine | +P |
| carbazole | + |
| azobenzene | + |
| 3,4-dihydroxybenzoic acid | −P |
| 4-methylmorpholine N-oxide | + |
| 3-cyanobenzoic acid | No flow |
| 4-nitrophenylacetic acid | No flow, at 0.1M, flow occurs lower concentrations (0.01–0.1M) |
| 2-(1H-benzotriazole-1-yl)-1,1,3,3-tetramethyluronium hexafluorophosphate (HBTU) | No flow, at 0.1M, flow occurs lower concentrations (0.01–0.1M) |
| 2,3-dichloro-5,6-dicyano-1,4-benzoquinone | + weak |
| tetrapropylammonium perruthenate | No flow |
| 1-oxo-2,2,6,6-tetramethylpiperdinium chloride | No flow |
| 5-benzimidazolecarboxylic acid | N.D.[δ] |
| 4-(aminomethyl) benzoic acid | N.D. |
| 4-(aminomethyl) benzoic acid | N.D. |
| N,N-diisopropylethylamine | N.D. |
| isobuylamine | N.D. |
| glutathione (SH) | N.D. |

*Those directional indicators ("+" or "−") followed by a "P" indicate that flow was achieved using a pulsed voltage program pursuant to FIG. 1, where $T_1$ 0.1–1 ms and $T_2$ = 3.0–10 ms.
[δ]"N.D.", in this table and the tables below, indicates either that the solute was immiscible with the solvent or that visual inspection suggested that it had decomposed.

The following solutions in DCM, at 0.1M unless otherwise indicated, have been tested:

| Reagent | Flow direction* |
|---|---|
| allylamine | − |
| butylamine | − |
| cyclohexylamine | − |
| 1-(3-aminopropyl) imidazole | − |
| diethylazodiacarboxylate | − |
| TP Palladium | − |
| isobutyiamine | − |
| isoamylamine | − |
| propylamine | − |
| 1 (3-aminopropyl)imidazole | − |
| p-carboxybenzenesulfonamide | N.D. |
| 2-(1H-benzotriazole-1-yl)-1,1,3,3-tetramethyluronium hexafluorophosphate (HBTU) | N.D. |

*Those directional indicators ("+" or "−") followed by a "P" indicate that flow was achieved using a pulsed voltage program pursuant to FIG. 1, where $T_1$ = 0.1–1 ms and $T_2$ = 3.0–10 ms.

The following solutions in methanol, all at 0.1M, have been tested:

| Reagent | Flow direction* |
|---|---|
| 4-fluorophenylacetic acid | – |
| 9-fluorenemethanol | –P |
| p-(methylthio) benzyl alcohol | – |
| (R) sec-phenethyl alcohol | – |
| 3-cyanobenzoic acid | No flow |
| 4-nitrophenylacetic acid | – weak |
| allylamine | No flow |
| 2-aminoethanol | No flow |
| 2-(1H-benzotriazole-1-yl)-1,1,3,3-tetramethyluronium hexafluorophosphate (HBTU) | N.D. |
| isobutylamine | N.D. |
| isomylamine | N.D. |

*Those directional indicators "+" or "–") followed by a "P" indicate that flow was achieved using a pulsed voltage program pursuant to FIG. 1, where $T_1$ = 0.1–1 ms and $T_2$ = 3.0–10 ms.

Example 2

An Electrode-pump Based Preferential Flow System

A channel system was fabricated on two inch by two inch by 20 mil plates of 211 Corning glass (Corning Glass Co., Corning, N.Y.) to confirm that liquids can be switched to a desired flow pathway by controlling the voltages applied to certain electrode-based pumps. As illustrated in FIGS. 11A and 11B, first channel 804 (2,600 μm long by 150 μm wide by 100 μm deep), second channel 805 (550 μm long by 100 μm wide by 100 μm deep), third channel 806 (800 μm long by 275 μm wide by 100 μm deep), fourth channel 807 (200 μm long by 100 μm wide by 100 μm deep), fifth channel 808 (550 μm long by 100 μm wide by 100 μm deep) and sixth channel 809 (2,600 μm long by 150 μm wide by 100 μm deep) were fabricated on channel plate 810 (not shown). Also fabricated on the channel plate 810 were first well 800A, second well 800B and third well 800C, which were connected by the channels. An electrode plate 820 was overlaid and sealed to the channel plate 810 by field assisted thermal bonding. The electrode plate 820 had openings into first well 800A and second well 800B (not illustrated). Third well 800C included a center drain 855. The electrode plate 820 further had platinum electrodes, fabricated by inserting 25 μm wires. The electrodes included first platinum electrode 801A, second platinum electrode 801B, third platinum electrode 801C, fourth platinum electrode 802A, fifth platinum electrode 802B, third platinum electrode 802C, and the two electrodes comprising gamma electrode-based pump 803. First platinum electrode 801A, second platinum electrode 801B and third platinum electrode 801C make up alpha electrode-based pump 801, while fourth platinum electrode 802A, fifth platinum electrode 802B and sixth electrode 802C make up beta electrode-based pump 802.

Figure 12A:
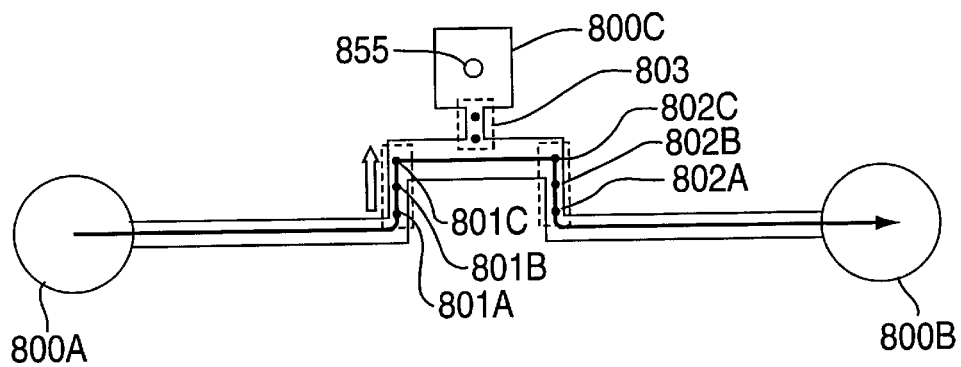
FIGS. 12A and 12B show a channel device having electrode-based pumps.
Figure 12B:
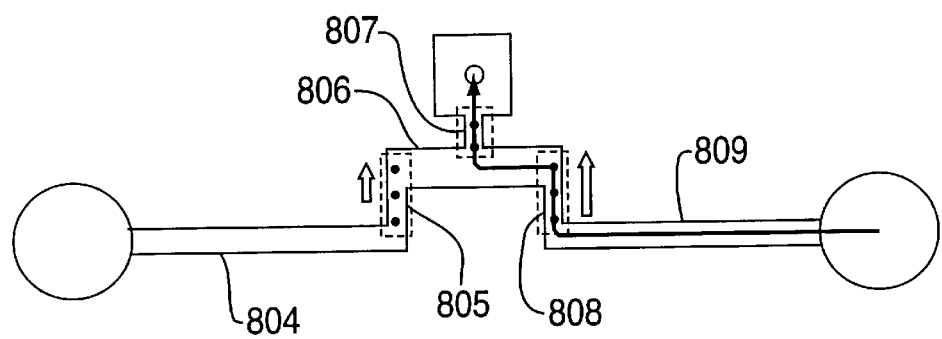

FIG. 12A shows methanol flowing from first well 800A to second well 800B, while bypassing third well 800C. This is done by applying 160 V to alpha electrode-based pump 801. FIG. 12B shows methanol flowing from second well 800B to third well 800C while bypassing first well 800A. This is done by applying 200 V to beta electrode-based pump 802, 100 V to gamma electrode-based pump 803 and 120 V to alpha electrode-based pump 801, where the polarity at beta and gamma electrode-based pumps 802 and 803 favored flow into the third well 800C, and the polarity at alpha electrode-based pump 801 favored flow away from first well 800A.

Example 3

Electrode-based Pumping Past Capillary Barriers

Figure 13:
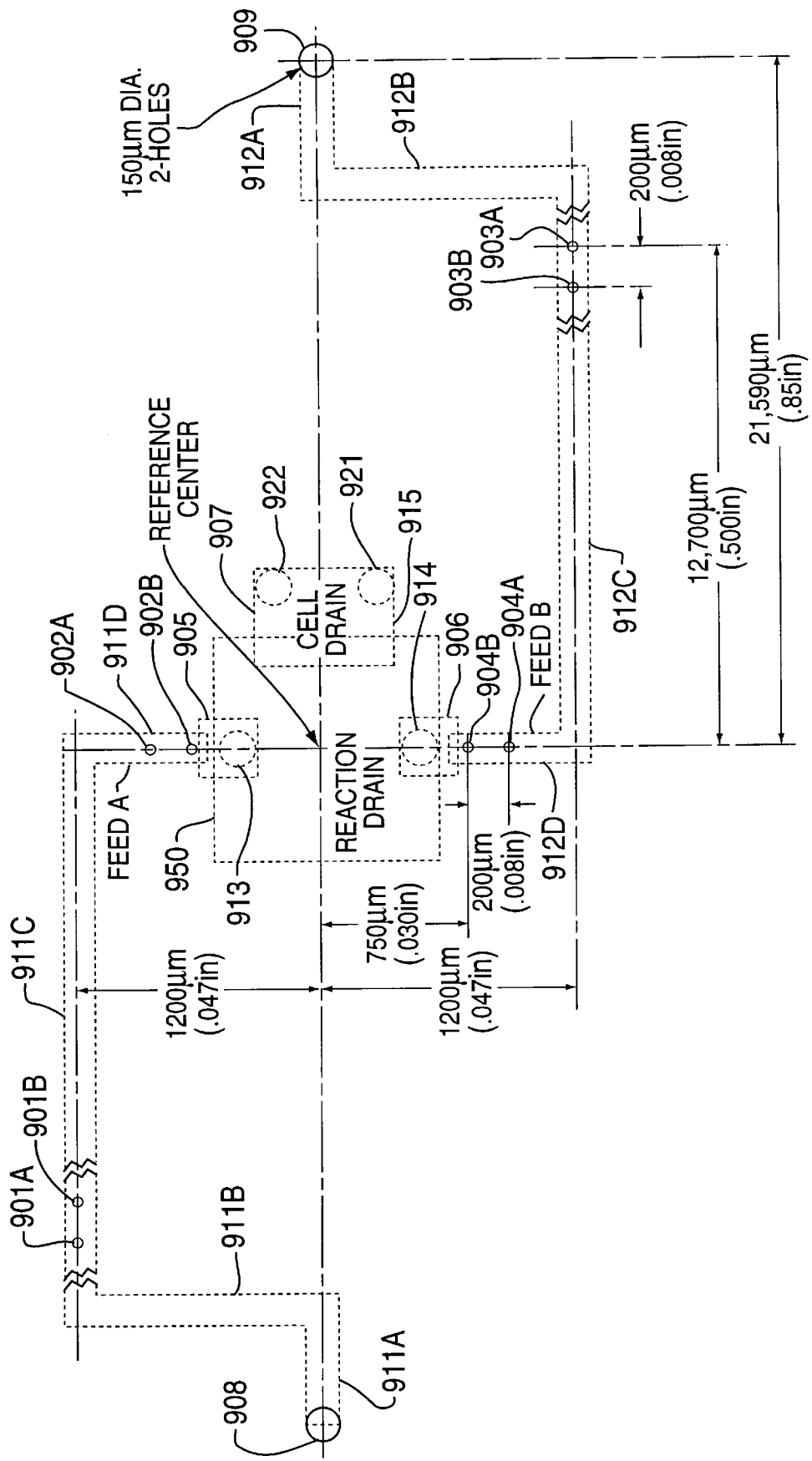
FIG. 13 shows a liquid distribution system design pursuant hydrologic liquid distribution system.

FIG. 13 shows a prototype liquid distribution system fabricated pursuant to the hydrologic liquid distribution system. The distribution system was constructed from three plates of Corning 7740 borosilicate glass, Corning Glass, Inc., Corning, N.Y. which plates became top plate 910, intermediate plate 920 and bottom plate 930. The top of intermediate plate 920 was coated with silicon as described above. In top plate 910 were formed, by laser drilling, first hole 901A, second hole 901B, third hole 902A, fourth hole 902B, fifth hole 903A, sixth hole 903B, seventh hole 904A and eighth hole 904B, which holes each had a diameter of 75 μm. First and second holes 901A and 901B were used to form first model electrode-based pump 961. Third and fourth holes 902A and 902B were used to form second prototype electrode-based pump 962. Fifth and sixth holes 903A and 903B were used to form third prototype electrode-based pump 963. Seventh and eighth holes 904A and 904B were used to form fourth model prototype electrode-based pump 964. The electrodes in each of first through fourth prototype electrode-based pumps, 961–964, were separated by 200 μm. By etching, alpha opening 905, beta opening 906 and gamma opening 907 were formed on the underside of top plate 910. By laser drilling, ninth hole 908 and tenth hole 909, each with a diameter of 150 μm, were formed through upper plate 910.

In intermediate plate 920 were formed first prototype channel 911 (made up of segments 911A–911D) and second prototype channel 912 (made up of segments 912A–912D). First and second prototype channels 911 and 912 having a depth of 80 μm and a width of 150 μm . The entries into these two prototype channels 911 and 912 are provided by ninth hole 908 and tenth hole 909, respectively. First reaction cell access hole 913 and second reaction cell access hole 914, each with a diameter of 150 μm , were laser drilled through the intermediate plate 920. In the underside of intermediate plate 920, a delta opening 915 was formed, which delta opening 915 connects the reaction cell 950 to first and second prototype drain holes 921 and 922.

In the bottom plate 930, the reaction cell 950 was formed by etching. First prototype drain hole 921 and second prototype drain hole 922 were laser drilled through bottom plate 920. The top plate 910 and intermediate plate 920 were bonded together by field assisted thermal onding.

When methanol was introduced into first prototype channel 911, the liquid was stopped from flowing into reaction cell access hole 913 by the capillary barrier formed by the structure at alpha opening 905. Correspondingly, the capillary barrier formed by the structure at beta opening 906 prevented methanol flow into the reaction cell access hole 914. Flow into the reaction cell access holes 913 or 914, by either route, could be initiated by activating the appropriate pumps. For instance, to pump methanol through first prototype channel 911, first prototype electrode-based pump 901 and second prototype electrode-based pump 902 were biased by applying 200 V. Flow through the prototype channel 911 was observed.

We claim:

1. A method of performing a chemical process in a liquid distribution apparatus that includes a substrate formed of two or more layers having reagent sources, reaction cells, channels of capillary dimensions, and electrode-based pumps, wherein at least a first said reagent source contains a first reagent, the channels provide fluid communication through the thickness of at least one substrate layer from said reagent sources to said reaction cells, and said electrode-based pumps comprise electrodes that contact the channels, the method comprising:

(a) applying a voltage across the electrodes of a first said pump that contacts a channel in order to move said first reagent into a reaction cell; and (b) contacting the first reagent with a second reagent that is in said reaction cell as part of said chemical process.

2. The method of claim 1, wherein the chemical process is a catabolic or anabolic reaction.

3. The method of claim 1, wherein the chemical process is a an oxidation or reduction.

4. The method of claim 3, wherein the chemical process is an oxidation and the first reagent is an m-chloroperbenzoic acid hydrogen peroxide, or $KMnO_4$.

5. The method of claim 3, wherein the chemical process is a reduction and the reagents are selected from the group consisting of $LiAlH_4$ and lithium borohydride.

6. The method of claim 1, wherein the process is an amide formation, a Mitsunobu reaction, a Suzuki coupling, a Stille coupling, an alkylation of an amine, an acylation of an amine, an alkylation of a ketone, a reductive amination, a sulfonamide formation, a DNA synthesis, a cycloaddition, a Mannich reaction, a Diels Alder reaction, a Wittig reaction, a Heck reaction, an elimination of a leaving group or a condensation reaction.

7. The method of claim 6, wherein the chemical process is amide formation and the reagents are selected from the group consisting of dehydration reagents, 2,3-dichloro-5,6-dicyano-1,4-benzoquinonone, protected amino acids, and N-methyl morpholine.

8. The method of claim 7, wherein the dehydration reagent is selected from o-benzotriazol-1-yl-N,N,N',N'-tetramethyluroniumhexafluorophosphate, 1-hydroxybenzotriazole hydrate, dicyclohexylcarbodiimide, and diisopropyl carbodiimide.

9. The method of claim 6, wherein the chemical process is a Mitsunobu reaction and the first reagent is a phenol, an alcohol, a diethylazodicarboxylate, a triphenylphosphine, or a N-methyl morpholine.

10. The method of claim 6, wherein the chemical process is Suzuki coupling and the first reagent is a halide, a palladium (0) catalyst, an aryl boronic acid, a triethyl amine, or a dimethyl formamide.

11. The method of claim 6, wherein the chemical process is Stille coupling and the reagents are selected from the group consisting of halide, palladium (0) catalyst, aryl stannate, N-methyl pyrrolidone and triphenyl arsine.

12. The method of claim 6, wherein the chemical process is alkylation or acylation of an amine and the reagents are selected from the group consisting of, tosylate compounds, halide compounds, amine compounds, N-methyl pyrrolidone, and phosgene.

13. The method of claim 6, wherein the chemical process is alkylation of a ketone and the reagents are selected from the group consisting of amine, ketone, lithium diiosopropyl amine, tetrahydrofuran, and alkyl iodide.

14. The method of claim 6, wherein the chemical process is reductive amination and the reagents are selected from the group consisting of amine, aldehyde, sodium cyanoborohydride, sodium triacetyoxyborohydride, borohydrate pyridine, and methylene chloride.

15. The method of claim 6, wherein the chemical process is sulfonamide formation and the reagents are selected from the group consisting of amines, sulfonyl chloride, and dimethylformamide.

16. The method of claim 6, wherein the chemical process is nucleic acid synthesis and the reagents are selected from the group consisting of oligonucleotides and phosphates.

17. The method of claim 6, wherein the chemical process is cycloaddition and the reagents are selected from the group consisting of peracids, substituted alkenes, diazo compounds, azide, nitrites, azomethine ylide, nitrones, and carbonyl oxides.

18. The method of claim 6, wherein the chemical process is a Mannich reaction and the reagents are selected from the group consisting of aldehydes, ketones, amine salts, amides, acids, and bases.

19. The method of claim 6, wherein the chemical process is a Diels Alder reaction and the reagents are selected from the group consisting of substituted alkenes and dienes.

20. The method of claim 6, wherein the chemical process is a Wittig reaction and the reagents are selected from the group consisting of triphenylphosphines and substituted alkenes.

21. The method of claim 6, wherein the chemical process is a Heck reaction and the reagents are selected from the group consisting of a palladium (0) catalyst, substituted alkenes, substituted halides, and triethylamines.

22. The method of claim 6, wherein the chemical process is elimination of a leaving group and the reagents are selected from the group consisting of alkyl and halides and bases.

23. The method of claim 1, wherein the chemical process is employed to synthesize a compound selected from the group consisting of a polymeric organic compound, an oligonucleotide, a peptide.

24. The method of claim 1, wherein the reagent is selected from the group consisting of carboxylic acids, carbodiimides, sulfonamides, amines, alcohols, pyridines, azodicarboxylates, carbazoles, azobenzenes, amino N-oxides, 1,4-benzoquinone and ammonium perruthenate.

25. The method of claim 1, wherein the second reagent is coupled to a solid support in the reaction cell.

26. The method of claim 25, wherein the solid support is one or more polymer beads.

27. The method of claim 1, wherein the apparatus further comprises a second reagent source containing a second reagent, and the method comprises applying a voltage across two said electrodes of a second pump to selectively move the second liquid into the reaction cell of step (a).

28. The method of claim 1 wherein the apparatus further comprises capillary barriers interposed in the channels to prevent liquid flow into the reaction cells in the absence of activating an associated electrode-based pump and wherein the voltage applied to two said electrodes of the first pump is effective to move the first reagent past a capillary barrier.

* * * * *